US006815569B1

(12) United States Patent
Dahl et al.

(10) Patent No.: US 6,815,569 B1
(45) Date of Patent: *Nov. 9, 2004

(54) COMPOSITIONS COMPRISING TETRAMANTANES AND PROCESSES FOR THEIR SEPARATION

(75) Inventors: Jeremy E. Dahl, Palo Alto, CA (US); Robert M. Carlson, Petaluma, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 391 days.

This patent is subject to a terminal disclaimer.

(21) Appl. No.: 10/012,545

(22) Filed: Dec. 12, 2001

Related U.S. Application Data

(60) Provisional application No. 60/300,148, filed on Jun. 21, 2001, and provisional application No. 60/262,842, filed on Jan. 19, 2001.

(51) Int. Cl.$^7$ .............................. C07C 13/28; C07C 7/00

(52) U.S. Cl. ........................... 585/352; 585/16; 585/21; 585/800; 585/802; 585/803; 117/68; 117/69; 117/70

(58) Field of Search .......................... 585/803, 21, 16, 585/800, 802, 352; 117/68, 69, 70

(56) References Cited

U.S. PATENT DOCUMENTS

| | | |
|---|---|---|
| 3,457,318 A | 7/1969 | Capaldi |
| 3,832,332 A | 8/1974 | Thompson |
| 4,952,748 A | 8/1990 | Alexander |
| 4,952,749 A | 8/1990 | Alexander |
| 4,952,757 A | 8/1990 | Purcell et al. |
| 4,982,049 A | 1/1991 | Alexander |
| 5,017,734 A | 5/1991 | Baum |
| 5,019,665 A | 5/1991 | Partridge |
| 5,245,104 A | 9/1993 | Cullick |
| 5,268,513 A | 12/1993 | Shen |
| 5,298,666 A | 3/1994 | Shen |
| 5,306,851 A * | 4/1994 | Wu et al. ............... 585/22 |
| 5,334,228 A * | 8/1994 | Ashjian et al. ............ 44/347 |
| 5,347,063 A | 9/1994 | Shen |
| 5,369,213 A | 11/1994 | Shen |
| 5,380,947 A | 1/1995 | Chen |
| 5,382,684 A | 1/1995 | Moini |
| 5,397,488 A | 3/1995 | Chen |
| 5,410,092 A | 4/1995 | Shen |
| 5,414,189 A * | 5/1995 | Chen et al. ............... 585/801 |
| 5,430,193 A | 7/1995 | Shen |
| 5,461,184 A | 10/1995 | Swanson |
| 5,498,812 A | 3/1996 | Bradway |
| 5,576,355 A | 11/1996 | Chen |
| 6,235,851 B1 | 5/2001 | Ishii |

FOREIGN PATENT DOCUMENTS

| | | |
|---|---|---|
| EP | 0399851 | 11/1996 |
| WO | WO 95/11472 | 4/1995 |

OTHER PUBLICATIONS

Aczel, et al., "Stability of Adamantane and its Derivatives to Coal–liquefaction Conditions, and its implications toward the organic structure of Coal", *Fuel*, vol. 58, pp. 228–230, (Mar. 1979).

Balaban, et al., Systemic Classification and Nomenclature of Diamond Hydrocarbons–I, *Tetrahedron, 34*, pp. 3599–3606, (1978), no month.

Badziag, P., et al., "Nanometre–sized Diamonds are More Stable than Graphite", *Nature*, vol. 343, pp. 244–245, and 517 (Jan. 1990).

Bagrii, Ye, et al., "Catalytic Breakdown of Paraffinic Hydrocarbons in the Presence of Adamantanes", *Petrol. Chem USSR*, vol. 30, No. 2, pp. 131–134, (1990), no month.

Chung, et al., Recent Development in High–Energy Density Liquid Fuels, *Energy and Fuels, 13*, pp. 641–649, (1999), no month.

Dahl, J., et al., Diamondoid Hydrocarbons as Indicators of Natural Oil Cracking, *Nature, 399*, pp. 54–57, (1999), no month.

Drexler, Eric K., *Nanosystems: Molecular Machinery Manufacturing and Computation*, John Wiley & Sons, pp. 238–249, (1992), no month.

Fort, Jr., et al., Adamantane: Consequences of the Diamondoid Structure, *Chem. Rev., 64*, pp. 277–300, (1964), no month.

Hala, V.S., et al., "Analyse Unds erwendung on Pyrolyseol", *Jahrgang*, pp. 85–87, (Feb. 1971) In German—English Abstract on p. 85, considered to extent of abstract.

Landa, S., "Adamantane and Its Homologues", *Current Science*, Gangalore, India, Vo. 32, pp. 485–489 (1963).

Lin, et al., Natural Occurence of Tetramantane ($C_{22}H_{36}$), Pentamantane ($C_{26}H_{32}$), and Hexamantane ($C_{30}H_{36}$) in a Deep Petroleum Reservoir, *Fuel*, 74:10, pp. 1512–1521, (1995).

McKervey, Synthetic Approaches to Large Diamondoid Hydrocarbons, *Tetrahedron, 36*, pp. 971–992, (1980).

Machacek, V., et al., "Let Od Objeveni Adamantanu", *Chemicke Listy/svazek*, pp. 753–761, (1982) Russian—English Abstract on p. 761, no month, considered to extent of abstract.

Oya, A, et al., "Carbonization of Adamantanes to a Graphitizable Carbon", *Fuel*, vol. 60, pp. 667–669, (Aug. 1981).

(List continued on next page.)

*Primary Examiner*—Elizabeth D. Wood
(74) *Attorney, Agent, or Firm*—Burns, Doane, Swecker, & Mathis, L.L.P.

(57) ABSTRACT

Disclosed are compositions comprising one or more tetramantanes. Specifically disclosed are compositions comprising 10 to 100 weight percent of one or more tetramantanes. Also disclosed are novel processes for the separation and isolation of tetramantane components into recoverable fractions from a feedstock containing at least a higher diamondoid component which contains one or more tetramantane components.

37 Claims, 24 Drawing Sheets

OTHER PUBLICATIONS

Petrov, A, "Hydrocarbons of Adamantane Series as Indicies of Petroleum Catagenesis Process", *Advances in Organic Geo Chemistry*, 6$^{th}$ International Meeting an Organic Geochemistry, pp. 517–522 (1973), no month.

Prusova, D., Liquid Chromatography of Adamantanes and Carbon Absorbents, *J. Chrom*, 234, pp. 1–11, (1982), no month.

Rollman, L. et al., "Adamantanes From Petroleum, with Zeolites", American Chemical Study, 210$^{th}$ ACS National Meeting, Abstract and paper, Aug. 20, 1995).

Sandia National Laboratories (2000), World's First Diamond Micromachines Created at Sandia, Press Release, (Feb. 22, 2000), www.Sandia.gov.

Schleyer, P., et al., "Nonacyclo[11.7.1.1$^{2,18}$.0$^{3,16}$.0$^{4,13}$.0$^{5,10}$.0$^{6,14}$.0$^{7,11}$.0$^{15,20}$]–Docosane, a Bastard Tetramantane", *J. of the Am. Chem. Soc.*, 90:8, letter to the editor, Aug. 28, 1968.

Shen, M., et al., Finite $T_d$ Symmetry Models for Diamond: From Adamantane to Superdamantane ($C_{35}H_{36}$), *J. Am., Chem. Soc.*, vol. 114, No. 2, pp 497–505, (1992), no month.

Supryadkina, NY, et al., "Catalytic Dealkylation of Alkyladamantanes", *Petrol. Chem., USSR*, vol. 28, No. 2, pp. 103–110, (1988), no month.

Tominaga, K., et al., "Next–generation Fine Chemicals Raw Material–Adamantane", *Chem Econ & Eng. Review*, vol. 17, No. 10, pp. 23–29, (Oct. 1985).

Vodicka, L, et al., "High Performance Liquid Chromatography of Halogeno Derivatives of Adamantane and Diamantane", *J. Chrom*, 270, pp. 199–205, (1983), no month.

Wingert, W., "G.c.–m.s. Analysis of Diamondoid Hydrocarbons in Smackover Petroleums", *Fuel*, vol. 71, pp. 37–42, (Jan. 1992).

Landa, S., "Adamantane and Its Homologues", *Current Science*, vol. 32, No. 11, pp. 485–489 (1963), no month.

* cited by examiner

● Feedstock B
■ Feedstock A

First Column

Fraction 33

Second Column

GC Retention Time (min.)

mirror plane

[121] Tetramantane     [123] Tetramantane     [1(2)3] Tetramantane
(ENANTIOMERS)

10A) Fraction #1 601 – 656 °F

10B) Fraction#2 656 – 702 °F

10C) Fraction#3 702 – 752 °F

10D) Fraction #4 752 – 800 °F

GC/MS time (minutes)

* non-diamondoid impurities

HPLC Fr. 6 (TIC)

Tetramantane (m/z 292)

[1(2)3] Tetramantane
*iso* Tetramantane
$C_{22}H_{28}$, $C_{3v}$ Symmetry
Molecular Weight = 292.466
Exact Molecular Weight = 292.2191010

Ball & Stick Representation

Carbon Framework

CPK Representation

[1(2)3] Tetramantane
*iso* Tetramantane
View into Specified Diamond Crystal Lattice Planes 111　　　110　　　100

[123] Tetramantane Enantiomer A
*skew* Tetramantane
$C_{22}H_{28}$, $C_2$ Symmetry
Molecular Weight = 292.466
Exact Molecular Weight = 292.2191010

Ball & Stick Representation

Carbon Framework

CPK Representation

[123] Tetramantane Enantiomer A
View into Specified Diamond Crystal Lattice Plane

|  111  |  110  |  100  |

[123] Tetramantane Enantiomer B
*skew* Tetramantane
$C_{22}H_{28}$, $C_2$ Symmetry
Molecular Weight = 292.466
Exact Molecular Weight = 292.2191010

Ball & Stick
Representation

Carbon
Framework

CPK
Representation

[123] Tetramantane Enantiomer B
View into Specified Diamond Crystal Lattice Plane 111  110  100

[121] Tetramantane
*anti* Tetramantane
$C_{22}H_{28}$, $C_{2h}$ (2/m) Symmetry
Molecular Weight = 292.466
Exact Molecular Weight = 292.2191010

Ball & Stick Representation

Carbon Framework

CPK Representation

[121] Tetramantane
View into Specified Diamond Crystal Lattice Plane 111   110   100

[1(2)3] Tetramantane (*iso*-Tetramantane)
Nonacyclo[9.7.1.1$^{1,5}$.1$^{1,9}$.1$^{3,17}$.1$^{7,15}$.0$^{5,16}$.0$^{9,14}$.0$^{13,18}$]docosane

M   P

[123] Tetramantane (*skew*-Tetramantane)
Nonacyclo[9.7.1.1$^{2,6}$.1$^{3,17}$.1$^{4,8}$.1$^{4,16}$.0$^{1,8}$.0$^{9,14}$.0$^{13,18}$]docosane

[121] Tetramantane (*anti*-Tetramantane)
Nonacyclo[11.7.1.1$^{6,18}$.0$^{1,16}$.0$^{2,11}$.0$^{3,8}$.0$^{4,19}$.0$^{8,17}$.1$^{10,15}$]docosane

A)

B)

COMPOSITIONS COMPRISING TETRAMANTANES AND PROCESSES FOR THEIR SEPARATION

REFERENCE TO RELATED APPLICATIONS

This application claims priority under 35 U.S.C. §119(e) to U.S. Provisional Application Ser. No. 60/262,842, filed Jan. 19, 2001 and to U.S. Provisional Application Ser. No. 60/300,148 filed Jun. 21, 2001, both of which are incorporated by reference.

BACKGROUND OF THE INVENTION

1. Field of the Invention

This invention is directed to novel compositions comprising one or more tetramantanes. This invention is also directed to novel processes for the separation and isolation of tetramantane components into recoverable fractions from a feedstock containing one or more tetramantane components.

2. References

The following publications and patents are cited in this application as superscript numbers:

[1] Lin, et al., *Natural Occurrence of Tetramantane ($C_{22}H_{28}$), Tetramantane ($C_{26}H_{32}$) and Hexamantane ($C_{30}H_{36}$) in a Deep Petroleum Reservoir*, Fuel, 74(10):1512–1521 (1995)

[2] Alexander, et al., Purification of Hydrocarbonaceous Fractions, U.S. Pat. No. 4,952,748, issued Aug. 28, 1990

[3] McKervey, *Synthetic Approaches to Large Diamondoid Hydrocarbons*, Tetrahedron, 36:971–992 (1980).

[4] Wu, et al., High Viscosity Index Lubricant Fluid, U.S. Pat. No. 5,306,851, issued Apr. 26, 1994.

[5] Chung et al., *Recent Development in High-Energy Density Liquid Fuels*, Energy and Fuels, 13; 641–649 (1999).

[6] Sandia National Laboratories (2000), *World's First Diamond Micromachines Created at Sandia*, Press Release, (Feb. 22, 2000) www.Sandia.gov.

[7] Balaban et al., *Systematic Classification and Nomenclature of Diamondoid Hydrocarbons-I, Tetrahedron*. 34, 3599–3606 (1978).

[8] Chen, et al., Isolation of High Purity Diamondoid Fractions and Components, U.S. Pat. No. 5,414,189 issued May 9, 1995.

All of the above publications and patents are herein incorporated by reference in their entirety to the same extent as if each individual publication or patent was specifically and individually indicated to be incorporated by reference in its entirety.

3. State of the Art

Tetramantanes are bridged-ring cycloalkanes having a molecular formula of $C_{22}H_{28}$. The compounds have a "diamondoid" topology, which means their carbon atom arrangement is superimposable on a fragment of the diamond lattice (FIG. 1). There are four possible tetramantane isomers, each possessing a different 3-dimensional structure: iso-tetramantane, anti-tetramantane and two enantiomers of skew-tetramantane (skew-tetramantane A and skew-tetramantane B). The anti- and skew-tetramantane each possess two quaternary carbon atoms while the iso- form has three quaternary carbon atoms (FIG. 7). Alternative naming systems proposed for these tetramantanes are [1(2)3] for iso-, [121] for anti-, and [123] A and B for skew- according to Balaban et al.[7]

Academic chemists have focused research on the interplay between physical and chemical properties of diamondoids. Lower diamoidids such as adamantane and diamantane, have been studied to elucidate structure-activity relationships in carbocations and radicals.[3] Process engineers have directed efforts toward removing diamondoids from hydrocarbon gas streams because these compounds cause problems during the production of hydrocarbonaceous materials by solidifying in pipes and other pieces of equipment[2].

The literature contains little information regarding the practical application of tetramantanes. This fact is probably due to extreme difficulties encountered in either their isolation or synthesis. Lin and Wilk, for example, discuss the presence of tetramantanes in a gas condensate.[1] The researchers postulate the existence of the compounds based on a mass spectrometry fragmentation pattern. They did not, however, report the isolation of a single tetramantane. McKervey et al. discuss an extremely low yielding synthesis of anti-tetramantane.[3] The procedure involves a complex starting material and employs drastic reaction conditions (e.g., gas phase on platinum at 360° C.).

Among other properties, diamondoids have by far the most thermodynamically stable structures of all possible hydrocarbons that possess their molecular formulas due to the fact that diamondoids have the same internal "crystalline lattice" structure as diamonds. It is well established that diamonds exhibit extremely high tensile strength, extremely low chemical reactivity, electrical resistivity greater than aluminum trioxide ($Al_2O_3$) and excellent thermal conductivity.

In addition, based on theoretical considerations, the tetramantanes have sizes in the nanometer range and, in view of the properties noted above, the inventors contemplate that such compounds would have utility in micro- and molecular-electronics and nanotechnology applications. In particular, the rigidity, strength, stability, thermal conductivity, variety of structural forms and multiple attachment sites shown by these molecules make possible accurate construction of robust, durable, precision devices with nanometer dimensions. The various tetramantanes are three-dimensional nanometer-sized units showing different diamond lattice arrangements. This translates into a variety of rigid shapes and sizes for the four tetramantanes. For example, [1(2)3] tetramantane is pedestal-shaped, [121] tetramantane has a block-like structure. The two enantiomers of [123] have left and right handed screw-like structures. It has been estimated that MicroElectroMechanical Systems (MEMs) constructed out of diamond should last 10,000 times longer than current polysilicon MEMs, and diamond is chemically benign and would not promote allergic reactions in biomedical applications.[6] Again, the inventors contemplate that tetramantane would have similar attractive properties. Furthermore, some of the isomers of tetramantane ([123] A and B) possess chirality, offering opportunities for making nanotechnology objects of great structural specificity with useful optical properties. Applications of these tetramantanes include molecular electronics, photonic devices, nanomechanical devices, nanostructured polymers and other materials.

In view of the above, there is an ongoing need in the art to provide for compositions comprising one or more tetramantanes, where anti-tetramantane is not the only tetramantane component in the compositions.

SUMMARY OF THE INVENTION

Accordingly, in one of its composition aspects, this invention is directed to a composition comprising one or more tetramantane components wherein said composition comprises at least about 50 weight percent tetramantane components based on the total weight of the diamondoids in the composition, where anti-tetramantane is not the only tetramantane component in the composition.

In another of its composition aspects, the compositions preferably comprise one or more tetramantane components wherein the tetramantane components make up from about 50 to 100 weight percent, preferably about 70 to 100 weight percent, more preferably about 90 to 100 weight percent and even more preferably about 95 to 100 weight percent of the total weight of the diamondoids in the compositions, where anti-tetramantane is not the only tetramantane component in the composition.

In another of its composition aspects, the compositions comprise at least about 10 weight percent and preferably at least about 20 weight percent of tetramantanes based on the total weight of the composition. Other compositions of this invention contain from 50 to 100 weight percent, 70 to 100 weight percent, 95 to 100 weight percent and 99 to 100 weight percent of tetramantanes based on the total weight of the composition, all again with the proviso that anti-tetramantane is not the only tetramantane component in the composition.

In another of its composition aspects, the compositions preferably comprise from about 70 to 100 weight percent, more preferably from about 90 to 100 weight percent, even more preferably from about 95 to 100 weight percent and most preferably from about 99 to 100 weight percent of a single tetramantane component, including isolated optical isomers thereof, based on the total weight of the composition, where the tetramantane is iso-tetramantane, skew-tetramantane or a single enantiomer of skew-tetramantane.

When tetramantane components are of a high purity, such tetramantane components can form crystals. Thus, this invention is directed to crystals of a skew or iso tetramantane component or of a mixture of two or more tetramantane components.

This invention is also directed to novel processes for the separation and isolation of tetramantane components into recoverable fractions from a feedstock containing one or more tetramantane components and nontetramantane materials. These processes for recovering a composition enriched in tetramantane components entail removing at least a portion of the nontetramantane materials which have a boiling point below the lowest boiling tetramantane component and utilizing a subsequent separation technique to recover tetramantane components from the resulting residue. Accordingly, this aspect is directed to processes which comprise:

a) selecting a feedstock comprising recoverable amounts of tetramantane components and nontetramantane materials;

b) removing from the feedstock a sufficient amount of nontetramantane materials that have boiling points below the boiling point of the lowest boiling point tetramantane component in the feedstock under conditions to form a treated feedstock enriched in tetramantane components which can be recovered;

c) recovering tetramantane components by separating said treated feedstock formed in b) above with one or more additional separation techniques selected from the group consisting of chromatographic techniques, thermal diffusion techniques, zone refining, progressive recrystallization and size separation techniques.

In one embodiment, after the step recited in b) the treated feedstock can be thermally treated to pyrolyze at least a sufficient amount of nondiamondoid components therefrom under conditions to provide a thermally treated feedstock retaining recoverable amounts of tetramantane. Such a pyrolization step prior to step c) is useful for thermally degrading at least a portion of any materials remaining in the treated feedstock having a thermal stability lower than the tetramantane components. This pyrolysis step can be carried out before step b) if desired.

BRIEF DESCRIPTION OF THE DRAWINGS

FIGS. 6(A, B) illustrates the preparative capillary gas chromatographic data for tetramantane isolations.

FIG. 12 above, displays the gas chromatograph of this feedstream.

DETAILED DESCRIPTION OF THE INVENTION

This invention is directed to compositions comprising one or more tetramantane components. However, prior to describing this invention in further detail, the following terms will first be defined.

Definitions

As used herein, the following terms have the following meanings.

Figure 1:
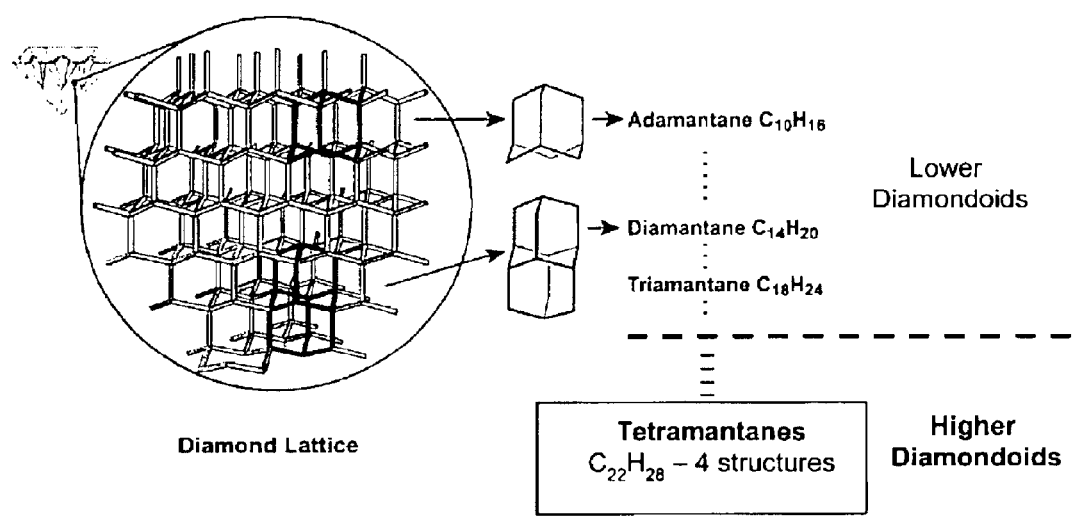
FIG. 1 illustrates the cage-shaped structure of diamondoids and their correlation to diamonds. Specifically, illustrated is the correlation of the structures of diamondoids to subunits of the diamond crystal lattice.

The term "diamondoids" refers to substituted and unsubstituted caged compounds of the adamantane series including adamantane, diamantane, triamantane, tetramantane, pentamantane, hexamantane, heptamantane, octamantane, nonamantane, decamantane, undecamantane, dodecamantane, and the like and also including all isomers and stereoisomers thereof. The compounds have a "diamondoid" topology, which means their carbon atom arrangement is superimposable on a fragment of the diamond lattice (FIG. 1). Substituted diamondoids comprise from 1 to 10 and preferably 1 to 4 independently-selected alkyl substituents. Diamondoids include "lower diamondoids," "tetramantanes," "higher diamondoids" and "nontetramantane higher diamondoids" as these terms are defined herein.

The term "tetramantanes" refers to diamondoids that are the face-fused tetramers of adamantane. There are four possible unsubstituted tetramantanes. Each of the tetramantane isomers possesses a different three-dimensional structure. Tetramantanes include "substituted" materials as described for diamondoids, generally.

The term "tetramantane component" refers to any single substituted or unsubstituted tetramantane, including optical isonomers (enantiomers).

The term "lower diamondoids" or "adamantane, diamantane and triamantane components" refers to adamantane, diamantane and triamantane and any and/or all unsubstituted and substituted derivatives of adamantane, diamantane and triamantane. These lower diamondoid components show no isomers or chirality and are readily synthesized, distinguishing them from "higher diamondoids".

The term "higher diamondoids" refers to any and/or all substituted and unsubstituted tetramantane components; to any and/or all substituted and unsubstituted pentamantane components; to any and/or all substituted and unsubstituted hexamantane components; to any and/or all substituted and unsubstituted heptamantane components; to any and/or all substituted and unsubstituted octamantane components; to any and/or all substituted and unsubstituted nonamantane components; to any and/or all substituted and unsubstituted decamantane components; to any and/or all substituted and unsubstituted undecamantane components; as well as mixtures of the above as well as isomers and stereoisomers of tetramantane, pentamantane, hexamantane, heptamantane, octamantane, nonamantane, decamantane, and undecamantane. Those higher diamondoids which are not tetramantane components are referred to as "nontetramantane higher diamondoids."

The term "feedstock" or "hydrocarbonaceous feedstock" refers to hydro-carbonaceous materials comprising recoverable amounts of one or more tetramantane components. Preferably, such feedstocks include gas condensates, refinery streams, and oil including oil derived from reservoir rocks, oil shale, tar sands, source rocks, and the like. Such feedstocks typically, but not necessarily, comprise lower diamondoids and other higher diamondoids as well as non-diamondoid components. Nondiamondoid components include materials boiling below and above the tetramantanes which exhibit atmospheric boiling points of about 370° to about 450° C. Typical feedstocks may also contain impurities such as sediment, metals including nickel and vanadium and other inorganics. They may also contain heteromolecules containing sulfur, nitrogen and the like. All of these materials which are not tetramantanes components are referred to as "nontetramantane materials."

The term "enriched" when used to describe the state of purity of one or more tetramantane components refers to such materials at least partially separated from nontetramantane materials, and in the case of "enriched" individual tetramantane components, from other tetramantane components so as to be at a concentration at least 25 and preferably at least 100 times as great as the concentration exhibited in a feedstock. Preferably "enriched" tetramantane or "enriched" tetramantane components make up at least 25%, especially at least 50% (i.e., 50–100%), more preferably at least 75% and yet more preferably at least 95% or even at least 99% by weight of the overall material in which they are present or in other words exhibit a weight purity of at least 25%, 50%, 75%, 95% or 99% of such material.

The term "remove" or "removing" refers to processes for removal of nondiamondoid components and/or lower diamondoid components from the feedstock. Such processes include, by way of example only, size separation techniques, distillation, evaporation either under normal or reduced pressure, well head separators, chromatography, chemical extraction, crystallization and the like. For example, Chen, et al.[8] disclose distillation processes for removing adamantane, substituted adamantane, diamantane, substituted diamantane, and triamantane from a hydrocarbonaceous feedstock. Size separation techniques include membrane separations, molecular sieves, gel permeation, size exclusion chromatography and the like.

The terms "distillation" and "distilling" refer to atmospheric, reduced pressure distillation, and elevated pressure distillation conducted to concentrate tetramantane components by removal of nontetramantane components from the feedstock based on boiling points. Unless otherwise specified, distillation temperatures are reported as atmospheric equivalents.

The terms "fractionation" and "fractionating" refer to processes in which materials in a mixture of materials are separated from each other such as by differential solubility, differential vapor pressure, differential chromatographic affinity and the like.

The terms "thermal degradation" and "pyrolytic processing" and the like refer to processes for treating a feedstock or a feedstock fraction at elevated temperature, to selectivity break down and/or pyrolyze at least a portion of nondiamondoid components in the feedstock or feedstock fraction.

The term "nondiamondoid components" refers to components of the feedstock that are not diamondoid in character wherein the term "diamondoid" is as defined herein.

The term "chromatography" refers to any of a number of well known chromatographic techniques including, by way of example only, column or gravity chromatography (either normal or reverse phase), gas chromatography, high performance liquid chromatography, and the like.

The term "alkyl" refers to straight and branched chain saturated aliphatic groups typically having from 1 to 20 carbon atoms, more preferably 1 to 6 atoms ("lower alkyls"), as well as cyclic saturated aliphatic groups typically having from 3 to 20 carbon atoms and preferably from 3 to 6 carbon atoms ("lower alkyls" as well). The terms "alkyl" and "lower alkyl" are exemplified by groups such as methyl, ethyl, propyl, butyl, isopropyl, isobutyl, sec-butyl, t-butyl, n-heptyl, octyl, cyclopropyl, cyclobutyl, cyclopentyl, cyclohexyl and the like.

Methodology

The enriched tetramantanes of this invention can be obtained from readily available feedstocks using the following general methods and procedures. It will be appreciated that where typical or preferred process conditions (i.e., reaction temperatures, times, solvents, pressures, etc.) are given, other process conditions can also be used unless otherwise stated. Optimum reaction conditions may vary with feedstocks, but such conditions can be determined by one skilled in the art by routine optimization procedures. Detailed descriptions of methods for processing feedstocks to enrich and isolate higher diamond compositions are set forth in U.S. Provisional Patent Application No. 60/262,842 filed Jan. 19, 2001 and U.S. Provisional Patent Application No. 60/300,148 filed Jun. 21, 2001. These applications are herein incorporated by reference in their entirety.

To obtain the tetramantane compositions described herein, a feedstock is selected such that said feedstock comprises recoverable amounts of tetramantane. Preferably, such feedstock comprises at least about 1 ppb of tetramantane components. It is understood, of course, that feedstocks having higher concentrations of tetramantanes facilitate recovery of these materials.

Preferred feedstocks include, for example, natural gas condensates and refinery streams having high concentrations of diamondoids. With regard to the latter, such refinery streams include hydrocarbonaceous streams recoverable from cracking processes, distillations, coking and the like. Particularly preferred feedstocks include natural gas condensates from the Norphlet Formation in the Gulf of Mexico and from the LeDuc Formation in Canada.

The feedstocks used to obtain the compositions of this invention typically comprise nondiamondoid components having boiling points both below and above the tetramantane components as well as lower diamondoids and nontetramantane higher diamondoids. A sufficient amount of these contaminants is removed from the feedstocks to provide treated feedstocks from which the tetramantane components can be enriched and recovered.

The removal of nondiamondoids, lower diamondoids and nontetramantane higher diamondoids can be carried out, by way of example only, using size separation techniques such as membranes, molecular sieves, etc., evaporation and thermal separators either under normal or reduced pressures, extractors, crystallization, chromatography, well head separators, and the like. A preferred separation method typically includes distillation of the feedstock to remove nondiamondoid components as well as nontetramantane diamondoids having boiling points less than that of the lowest boiling point tetramantane component. Temperature profiles for distillation runs and the resulting distillation cuts can be determined on the basis of the tetramantane component of interest. Preferably, the feedstock is distilled to provide cuts above and below about 335° C., atmospheric equivalent boiling point, more preferably, above and below about 345° C. atmospheric equivalent boiling point and more preferably, above and below about 370° C. atmospheric equivalent boiling point. In each instance, the lower cuts, which are enriched in lower diamondoids and low boiling point nondiamondoid components, are discarded. Distillation can be operated to provide several cuts in the temperature range of interest to provide the initial isolation of the identified tetramantane. The cuts, which are enriched in tetramantane or a particular tetramantane component of interest, are retained and may require further purification. For recovery of tetramantanes, the preferred distillation cuts are taken at atmosphere equivalent boiling point temperatures of from 300° to about 430° C., preferably from 330° to about 400° C., and especially 350° to 380° C. Additional temperature refinements will allow for higher purity cuts for the tetramantane of interest. Other methods for the removal of contaminants and further purification of an enriched tetramantane fraction can additionally include the following nonlimiting examples: size separation techniques, evaporation either under normal or reduced pressure, crystallization, chromatography, well head separators, reduced pressure and the like.

The contaminant removal may also include a thermal degradation step either prior to or subsequent to distillation. Thermal degradation is an effective method to remove hydrocarbonaceous, nondiamondoid components from the feedstock. It is effected by heating the feedstock under vacuum or 400° C. (preferably about 410° C. to about 475°

C., most preferably about 410° C. to about 450° C. for from 5 to 30 hours). The specific conditions employed are selected such that recoverable amounts of tetramantane components are retained in the feedstock. The selection of such conditions is well within the skill of the art. Preferably, thermal degradation is continued for a sufficient period of time and at a sufficiently high enough temperature to thermally degrade at least about 10% by weight of the nondiamondoids components of the feed material prior to thermal degradation. More preferably at least 50% and even more preferably at least 90% of the nondiamondoids are thermally degraded.

Thermal degradation, while a useful embodiment, is not always necessary to facilitate the recovery, isolation or purification of the tetramantane components. Other separation methods may allow for the concentration of these tetramantane components to be sufficiently high in certain feedstocks that direct purification methods such as chromatography including preparative gas chromatography and high performance liquid chromatography and crystallization may be used to isolate tetramantane components.

Even after distillation or thermal degradation/distillation, further purification of the tetramantane components may be desired to provide the compositions of this invention. One may use purification techniques such as chromatography, crystallization, thermal diffusion techniques, zone refining, progressive recrystallization, size separation and the like. For instance, the treated feedstock can be subjected to one or more of the following additional procedures: 1) gravity column chromatography using silver nitrate impregnated silica gel; 2) multicolumn preparative capillary gas chromatography; 3) single column high performance liquid chromatography; 4) high performance liquid chromatography with multiple columns of differing selectivity; and 5) crystallization to provide crystals of the highly concentrated tetramantanes. These provisions can be combined. For example, preparative capillary gas chromatography can be coupled with high performance liquid chromatography as a first or subsequent separation method.

Further processing using these methods allow for more refined separations which can lead to a pure tetramantane component. Enantioselective (chiral) stationary phases have been applied in chromatographic methods to effectuate further separations. High performance liquid chromatography methods also offer the possibility of using chiral solvents or additives to achieve resolution of enantiomers.

For example, separation of enantiomeric forms of the tetramantanes can be achieved using several approaches. One such approach is spontaneous crystallization with resolution and mechanical separation. This approach to enantiomer resolution can be enhanced by preparation of derivatives or by the use of additives, chiral solvents, or various types of seed crystals.

Another resolution option is chemical separation under kinetic or thermodynamic control. Other suitable processes for enantiomers resolution include chiral separations, which can be preformed using a gas chromatographic (GC) see "Chiral Chromatography", T. E. Beesley, et. al, Wiley, Johnson & Sons, January 1998, incorporated herein by reference, by high performance liquid chromatographic (HPLC) and by supercritical fluid chromatographic (SFC) techniques, see "Supercritical fluids in Chromatography and Extraction", R. M. Smith, Elsevier Science, December 1997, incorporated herein by reference.

Compositions

This invention is directed to compositions comprising one or more tetramantane components wherein said compositions comprise at least about 50 weight percent tetramantane components based on the total weight of the diamondoids in the compositions. The compositions preferably comprise from about 70 to about 100 weight percent, more preferably about 90 to 100 weight percent and even more preferably about 95 to 100 weight percent tetramantane components based on the total weight of the diamondoids in the composition.

Such tetramantane-enriched compositions are obtained through the series of unit operations described above which can be used to concentrate tetramantanes to at least 25 times and more preferably at least 100 times the levels at which they occur in readily-available feedstocks. The total weight percent of tetramantane components in the compositions is preferably at least 10% by weight based upon the total weight of the composition. In a more preferred aspect the total weight percent of tetramantane components is from 50 to 100 weight percent, more preferably 70 to 100 weight percent and even more preferably 95 or 99 to 100 weight percent based upon the total weight percent of the composition.

In other aspects, the compositions comprise an enriched individual tetramantane component such that they contain from 70 to 100 weight percent, more preferably from 90 to 100 weight percent, even more preferably from 95 to 100 weight percent and most preferably from 99 to 100 weight percent of a single tetramantane component including isolated optical isomers thereof, again with the proviso that the single tetramantane component is not anti-tetramantane.

This invention is also directed to mixtures of these four tetramantane components, as well as substituted tetramantane components alone or together with nonsubstituted materials.

At the high tetramantane concentrations and purities achieved by the present invention, tetramantane components can form crystals. Accordingly, another aspect of this invention is directed to tetramantane crystals, whether crystals of a single tetramantane component, co-crystals comprising crystals of at least two tetramantane components or co-crystals of tetramantane components with other higher diamondoids, such as tetramantane components.

The tetramantanes recovered and isolated in this invention include substituted tetramantane components. These naturally-occurring substituted tetramantanes have similar properties to the unsubstituted tetramantane components described herein and are present in the feedstocks. Substituted tetramantanes may act as useful intermediates in various tetramantane applications or can be de-alkylated to yield the corresponding unsubstituted tetramantanes. Substituted tetramantanes contain 1 to 10 alkyl substituents, and more preferably 1 to 4 such substituents.

The most prevalent substituted tetramantanes in the feedstocks used are tetramantanes substituted with lower alkyls. The most prevalent of these are methyl and ethyl-substituted tetramantanes, including methyl, ethyl, dimethyl, and trimethyl tetramantanes.

Utility

These tetramantane-containing compositions are useful in micro- and molecular-electronics and nanotechnology applications. In particular, the rigidity, strength, stability, thermal conductivity, variety of structural forms and multiple attachment sites shown by tetramantanes makes possible accurate construction of robust, durable, precision devices with nanometer dimensions. These special structural characteristics set these compounds apart from acyclic molecules, from condensed-ring systems and even from bridged-ring counterparts. The great stability, nanometer size, variable yet rigid geometry, well defined distances for places of attachment, nonplanar bridgeheads lead to their unique features. Due to the rigidity, specialized geometry, 3-dimensional shape and nanometer size of the tetramantane components, it is expected that molecular aggregates and building blocks comprising them will enable construction and synthesis of a unprecedented array of desirable materials that will find applications in molecular electronic computing devices, reduced-size machines such as molecular robots and self-replicating manufacturing systems. Alternatively, the tetramantanes may be used as novel materials of construction with special chemical, optical, electric and thermal conductivity properties for coatings, film layering and other applications taking advantage of the diamond-like properties, etc.

In addition, tetramantane-containing compositions can also be used in a high-quality lubricant which exhibits a high Viscosity Index and a very low pour point.[4] When so employed, these lubricants comprise from about 0.1 to 10 weight percent tetramantanes.

Still further, these tetramantane-containing compositions can be used as high density fuels in the manner described by Chung, et al.[5], incorporated herein by reference.

The following examples are offered to illustrate this invention and are not to be construed in any way as limiting the scope of this invention. Unless otherwise stated, all temperatures are in degrees Celsius.

As used herein and in the Figures, the following abbreviations have the following meanings. Any abbreviation not defined below has its generally accepted meaning.

| API = | American Petroleum Institute |
|---|---|
| ATM EQV = | atmospheric equivalent |
| EOR Traps = | end of run traps |
| FID = | flame ionization detector |
| G = | grams |
| GC = | gas chromatography |
| GC/MS = | gas chromatography/mass spectroscopy |
| HPLC = | high performance liquid chromatography |
| HYD RDG = | hydrometer reading |
| MIN = | minute |
| ML = | milliliters |
| ODS = | octadecylsilane |
| pA = | pico amps |
| ppb = | parts per billion |
| RI = | refractive index |
| SFC = | super critical fluid chromatography |
| SIM DIS = | simulated distillation |
| ST = | start |
| TIC = | total ion current |
| VLT = | vapor line temperature |
| VOL PCT = | volume percent |
| WT PCT = | weight percent |

EXAMPLES

Example 1

Isolation of Tetramantane Components

The purpose of this example is to demonstrate procedures for the isolation of four tetramantane component isomers. These procedures did not employ a pyrolysis step. After removal of lower boiling point nontetramantane components (including some lower diamondoids and tetramantanes from the feedstock by distillation), the tetramantane components in this example were recovered by chromatography and crystallization. The distillation preferably can be operated to provide specific cuts, thus removing both lower and higher boiling point components, leaving only components within a desired boiling point range.

Figure 2:
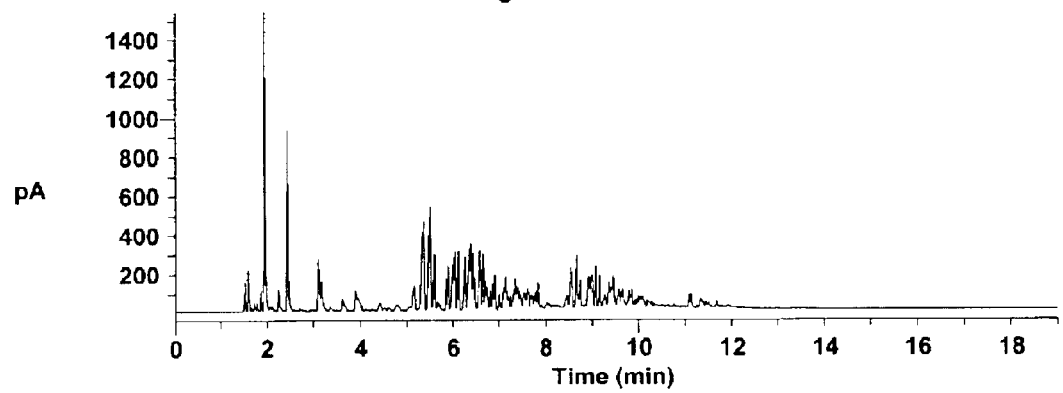
FIG. 2 illustrates the gas chromatogram of a gas condensate feedstock; one of the original feedstocks used in the Examples (Feedstock A). Tetramantanes are present in low concentrations, barely detectable, but are shown in vacuum distillate fraction (FIG. 5).
Figure 3:
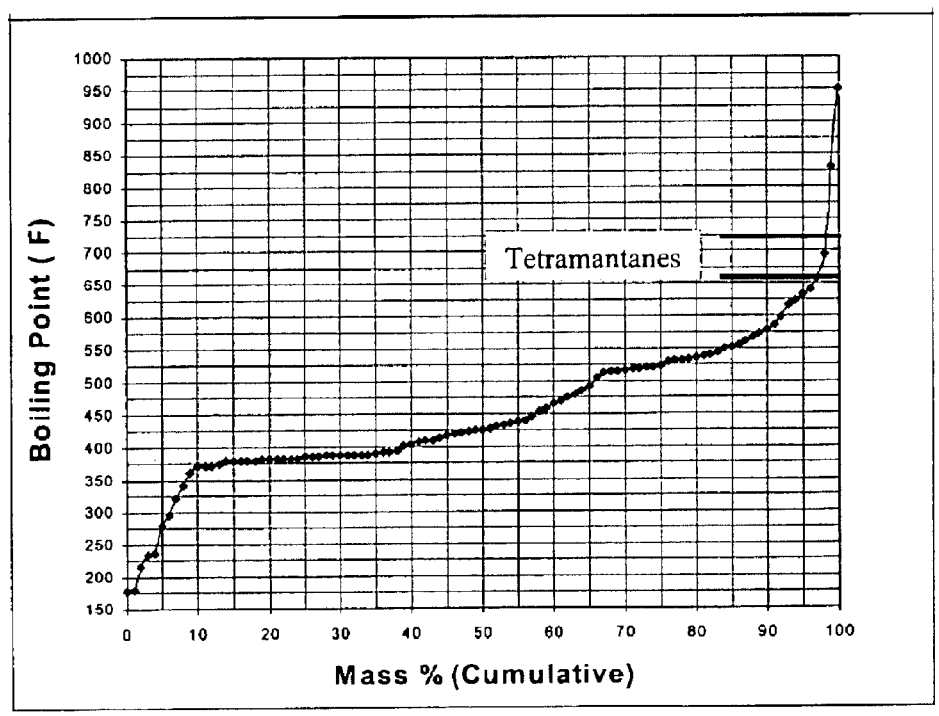
FIG. 3 illustrates a simulated distillation profile of a gas condensate feedstock containing petroleum byproducts used in the Examples (Feedstock B). Boiling points depicted are atmospheric equivalents.

Step 1:

Suitable starting materials were obtained. These materials included a gas condensate, Feedstock A (a gas chromatogram of this material is depicted in FIG. 2), and a gas condensate containing petroleum byproducts Feedstock B (a high temperature simulated distillation profile of this type of material is depicted in FIG. 3). Although other condensates, petroleums, or refinery cuts and products could have been used, these two materials were chosen due to their high concentration of higher diamondoids (0.3 weight percent), as determined by GC and GC/MS. Both feedstocks were light colored and had API gravities between 19 and 20° API.

Step 2:

Samples from Feedstocks A and B were distilled into a number of fractions based on boiling points to separate the lower boiling point components (nondiamondoids and lower diamondoids) and to further concentrate and enrich tetramantanes in various fractions. The yields of atmospheric distillate fractions of two separate samples of Feedstock B are shown in Table 1, below and are contrasted to the simulated distillation yields calculated for that feedstock. As seen from Table 1, the simulation data are in agreement with the distillation data.

TABLE 1

Yields of Atmospheric Distillation Fractions from Two Separate Runs of Feedstock B

| Cut (° F.) | Sim Dis Est.'d Yields (Wt %) | Feedstock B Yields (Wt %) | Difference |
|---|---|---|---|
| | | (Run 2) | |
| To 349 | 8.0 | 7.6 | 0.4 |
| 349 to 491 | 57.0 | 57.7 | −0.7 |
| 491 to 643 | 31.0 | 30.6 | 0.4 |
| 643 and higher | 4.0 | 4.1 | −0.1 |
| | | (Run 1) | |
| To 477 | 63.2 | 59.3 | 3.9 |
| 477 to 515 | 4.8 | 7.3 | −2.5 |
| 515 to 649 | 28.5 | 31.2 | −2.7 |
| 649 and higher | 3.5 | 2.1 | 1.4 |

Figure 4:
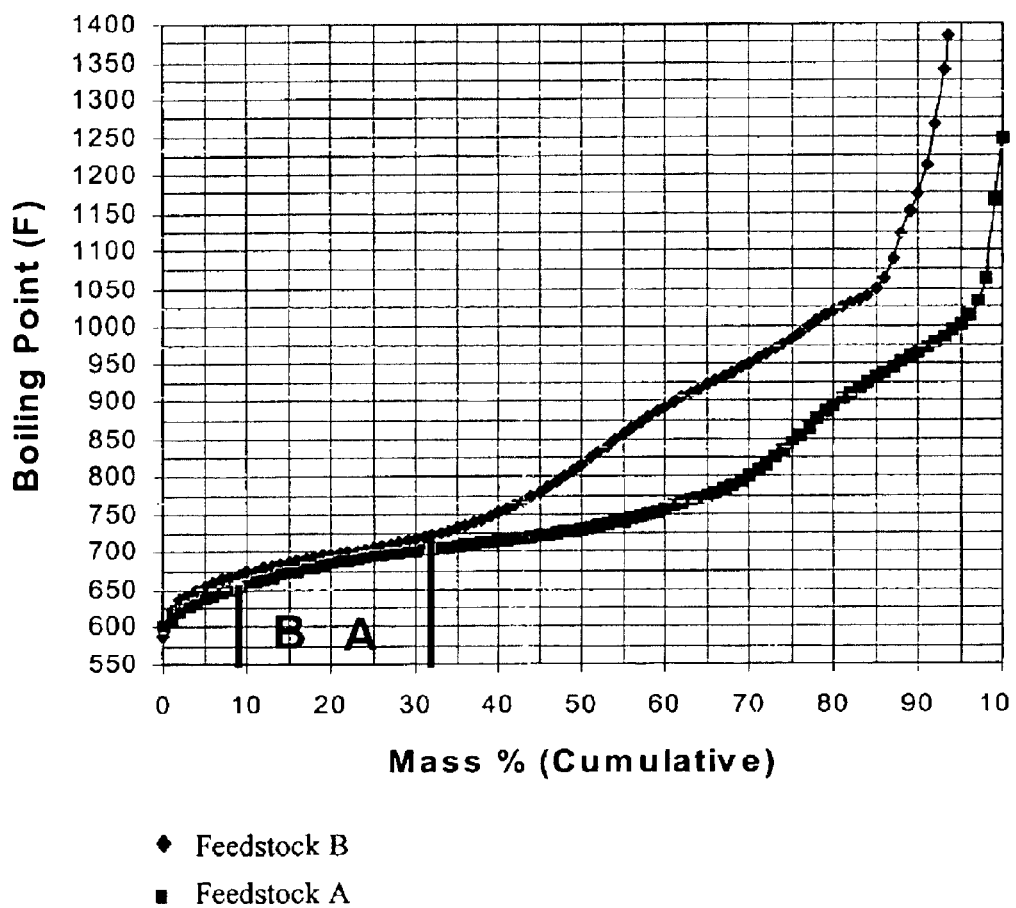
FIG. 4 illustrates a high temperature simulated distillation profile of atmospheric residue of diamondoid rich gas condensates; Feedstock A and Feedstock B.

The higher diamondoid-containing atmospheric residue fraction from Feedstock B was in the 2 to 4 weight percent range as shown in Table 1. FIG. 4 compares a high-temperature simulated distillation profile of the atmospheric residue of the gas condensates, Feedstock A and Feedstock B. Additionally outlined is the identified location and size of the tetramantane-containing fractions. In terms of atmospheric equivalent boiling points the tetramantanes were anticipated to be predominately within the range of 300 to about 430° F. with a large portion within the range of 330 to about 400° F. The lower mass percent shown for the tetramantane-containing fractions of Feedstock B, as compared to Feedstock A was due to nondiamondoid materials in Feedstock B. The nondiamondoid material can be removed by subsequent processes such as pyrolysis.

Figure 5:
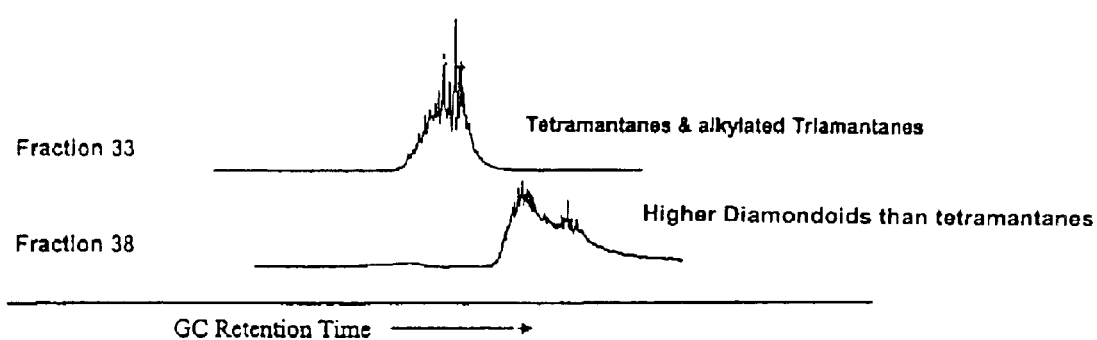
FIG. 5 illustrates gas chromatographic profiles of a distillate fraction containing tetramantanes from a gas condensate, Feedstock A.

A sample of gas condensate, Feedstock A was distilled into 38 fractions to remove lower diamondoids and concentrate higher diamondoids including tetramantanes as verified by GC (see FIG. 5). Fraction 33 was a recovered distillate, containing tetramantane components and alkylated triamantanes boiling in the range 650 to 700° F. The boiling points of fractions are given as atmospheric equivalent temperatures, however, the actual distillation can occur at other pressures and corresponding temperatures.

Figure 9:
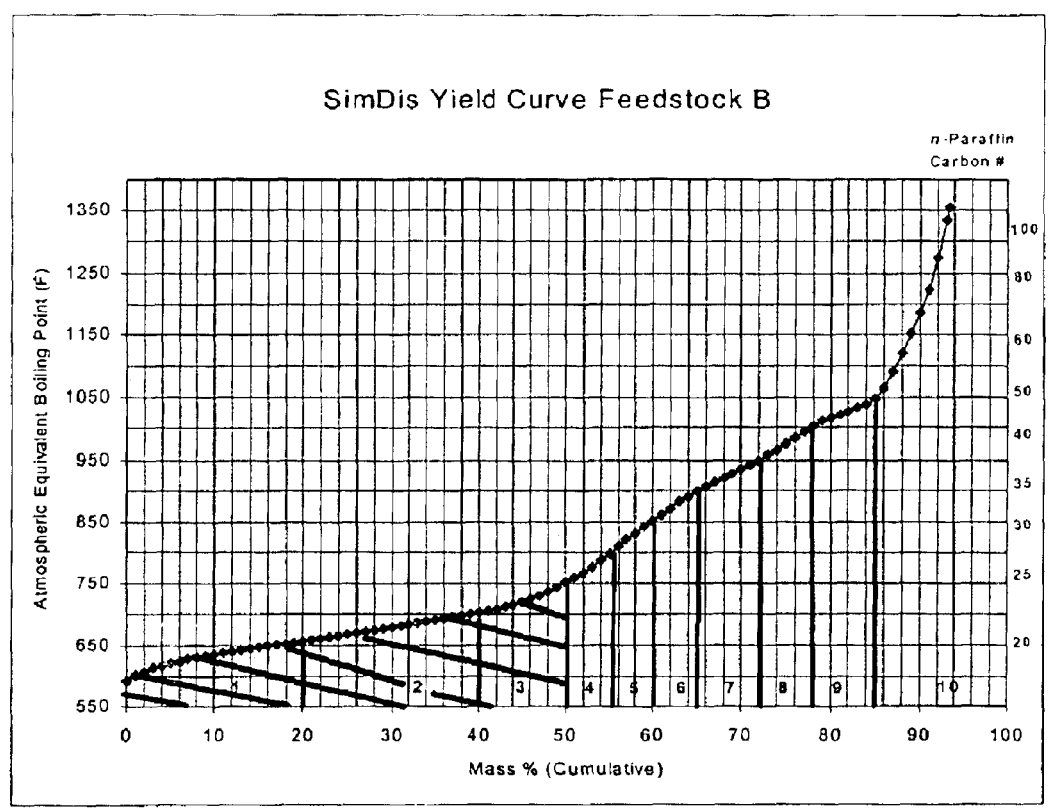
FIG. 9 illustrates a high temperature simulated distillation profile of Feedstock B using the atmospheric distillation 650° F.+bottoms as feedstock. This FIG. also illustrates the targeted cut points (1–10) for diamondoid isolations. Tetramantanes are contained primarily in distillate fractions 1 through 3.
Figure 10:
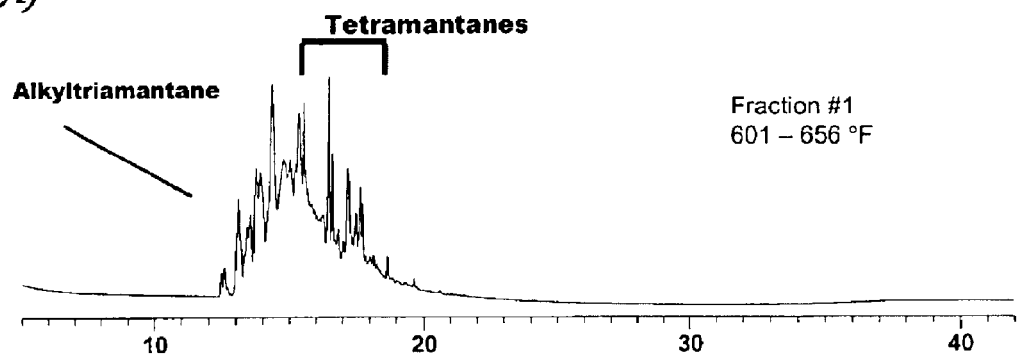
FIGS. 10(A, B, C, D) illustrates the gas chromatograms of distillate Fractions #1, #2, and #3 of Feedstock B atmospheric distillation 650° F.+bottoms illustrated in FIG. 9 and exemplified in Example 1.
Figure 10:
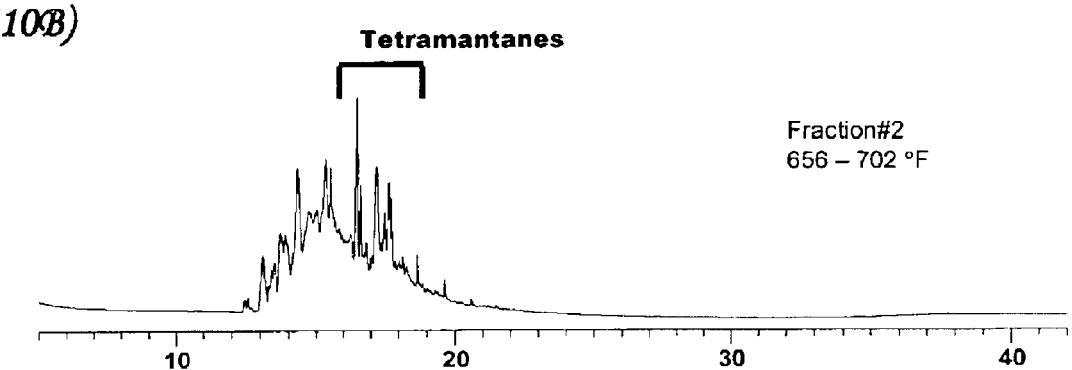
Figure 10:
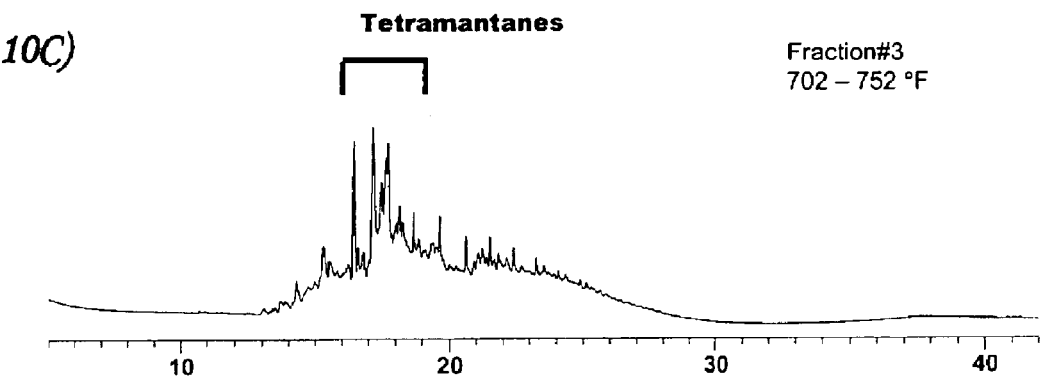
Figure 10:
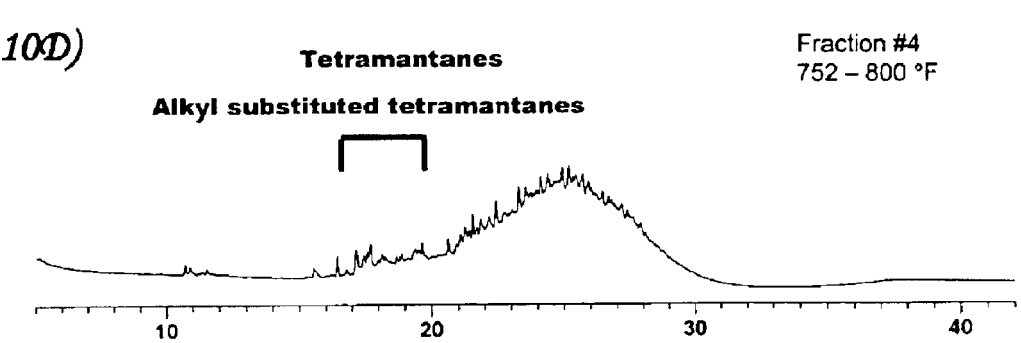

Additionally, Feedstock B was distilled into fractions containing higher diamondoids guided by a high-temperature simulated-distillation curve (FIG. 9). Comparison of FIGS. 5 and 10 shows that Feedstock B contained impurities not present in Feedstock A. The feed to the high temperature distillation process was the atmospheric (650° F.+) bottoms. Complete Feedstock B distillation reports are given in Tables 2A&B. Tables 3A&B, illustrate the distillation reports for Feedstock B 643° F.+distillation bottoms.

TABLE 2A

Distillation Report for Feedstock B
(FSL # 8471)
Feedstock B
Column Used: Clean 9" × 1.4" Protruded Packed

| CUT | VAPOR TEMP ° F. ST–END | DISTILLATION RECORD | | | | NORMALIZED | | ACTUAL | |
|---|---|---|---|---|---|---|---|---|---|
| | | WEIGHT G | VOLUME ml @ 60° F. | API 60/60 | DENSITY @ 60° F. | WT PCT | VOL PCT | WT PCT | VOL PCT |
| 1 | 226–349 | 67.0 | 80 | 38.0 | 0.8348 | 7.61 | 8.54 | 7.39 | 8.26 |
| 2 | 349–491 | 507.7 | 554 | 22.8 | 0.9170 | 57.65 | 59.12 | 55.98 | 57.23 |
| 3 | 491–643 | 269.6 | 268 | 9.1 | 1.0064 | 30.62 | 28.60 | 29.73 | 27.69 |
| COL HOLDUP | | 0.2 | 0 | 6.6 | 1.0246 | 0.02 | 0.00 | 0.02 | 0.00 |
| BTMS | 643+ | 36.1 | 35 | 6.6 | 1.0246 | 4.09 | 3.74 | 3.98 | 3.62 |
| EOR TRAPS | | 0.0 | 0 | | | 0.00 | 0.00 | | 0.00 |
| TOTALS | | 880.6 | 937 | | | 100.00 | 100.00 | 97.09 | 96.80 |
| LOSS | | 26.4 | 31 | | | | | 2.91 | 3.20 |
| FEED | | 907.0 | 968 | 19.5 | 0.9371 | | | 100.00 | 100.00 |
| BACK CALCULATED API AND DENSITY | | | | 19.1 | 0.9396 | | | | |

TABLE 2B

Distillation Report for Feedstock B
(FSL # 8471)
Feedstock B
Column Used: Clean 9" × 1.4" Protruded Packed

| TEMPERATURE DEGREES F. | | | | | | | API GRAVITIES | | |
|---|---|---|---|---|---|---|---|---|---|
| VAPOR | | | | | | | | OBSERVED | |
| VLT | ATM EQV. | POT | PRESSURE TORR | REFLUX RATIO | CUT NO | VOLUME ml @ 60° F. | WEIGHT G | HYD RDG | TEMP ° F. | 60° F. |
| 93 | 225.8 | 262 | 50.000 | 3:1 | | START OVERHEAD | | | | |
| 198 | 349.1 | 277 | 50.000 | 3:1 | 1 | 80 | 67.0 | 39.6 | 80.0 | 38.0 |
| 321 | 490.8 | 376 | 50.000 | 3:1 | 2 | 554 | 507.7 | 24.1 | 80.0 | 22.8 |
| | | | Cut 2 looks Milky, White crystals form in Run Down Line. Heat Lamp applied to drip tube. | | | | | | | |
| | | | Cool to transfer btms to smaller flask. | | | | | | | |
| 208 | 437.7 | 323 | 10.000 | 3:1 | | START OVERHEAD | | | | |
| 378 | 643.3 | 550 | 10.000 | 3:1 | 3 | 268 | 269.6 | 9.9 | 75.0 | 9.1 |
| | | | Shutdown due to dry pot | | | | | | | |
| | | | END OF RUN TRAPS | | | 0 | 0.0 | | | |
| | | | VOLUME DISTILLED | | | 902 | | | | |
| | | | COLUMN HOLDUP | | | 0 | 0.2 | 0.0 | 0.0 | 6.6 |
| | | | BOTTOMS | | | 35 | 36.1 | 7.2 | 72.0 | 6.6 |
| | | | RECOVERED | | | 937 | 880.6 | | | |
| | | | FEED CHARGED | | | 968 | 907.0 | 20.7 | 80.0 | 19.5 |
| | | | LOSS | | | 31 | 26.4 | | | |

TABLE 3A

Vacuum Distillation Report for Feedstock B
(FSL # 8691)
Feedstock B — Atmospheric distillation resid 650° F. + bottoms
Column Used: Sarnia Hi Vac

| | TEMPERATURE DEGREES F. | | | | | | | | API GRAVITIES | |
| --- | --- | --- | --- | --- | --- | --- | --- | --- | --- | --- |
| | VAPOR | | | | | VOL | | | OBSERVED | |
| VLT | ATM EQV. | POT | PRESSURE TORR | REFLUX RATIO | CUT NO | ml 60° F. | WEIGHT G | HYD RDG | TEMP ° F. | 60° F. |
| 315 | 601.4 | 350 | 5.000 | | | | START OVERHEAD | | | |
| 344 | 636.8 | 382 | 5.000 | | | 300 | READING | | | |
| 342 | 644.9 | 389 | 4.000 | | | 500 | READING | | | |
| 344 | 656.3 | 395 | 3.300 | | 1 | 639 | 666.4 | 7.8 | 138.0 | 4.1 |
| 353 | 680.1 | 411 | 2.500 | | | 400 | READING | | | |
| 364 | 701.6 | 430 | 2.100 | | 2 | 646 | 666.9 | 9.4 | 138.0 | 5.6 |
| 333 | 736.0 | 419 | 0.400 | | | 200 | READING | | | |
| 336 | 751.9 | 432 | 0.300 | | 3 | 330 | 334.3 | 12.4 | 139.0 | 8.3 |
| 391 | 799.9 | 468 | 0.500 | | 4 | 173 | 167.7 | 19.0 | 139.0 | 14.5 |
| 411 | 851.6 | 500 | 0.270 | | 5 | 181 | 167.3 | 26.8 | 139.0 | 21.7 |
| 460 | 899.8 | 538 | 0.360 | | 6 | 181 | 167.1 | 27.0 | 139.0 | 21.9 |
| 484 | 950.3 | 569 | 0.222 | | 7 | 257 | 238.4 | 26.2 | 139.0 | 21.2 |
| Shut down distillation to check pot temperature limits with customer. (Drained trap material 5.3 grams) | | | | | | | | | | |
| 472 | 935.7 | 576 | 0.222 | | | | START OVERHEAD | | | |
| 521 | 976.3 | 595 | 0.340 | | 8 | 91 | 85.4 | 23.7 | 139.0 | 18.9 |
| 527 | 999.9 | 610 | 0.235 | | 9 | 85 | 80.8 | 23.0 | 139.0 | 18.2 |
| 527 | 1025.6 | 624 | 0.130 | | 10 | 98 | 93.8 | 21.6 | 139.0 | 16.9 |
| Drained remaining trap material of 16.5 grams (~4 grams of water) | | | | | | | | | | |
| | | MID AND | END OF RUN TRAPS | | | 20 | 17.8 | (mathematically combined) | | |
| | | | VOLUME DISTILLED | | | 2701 | | | | |
| | | | COLUMN HOLDUP | | | 4 | 4.0 | 0.0 | 0.0 | 3.4 |
| | | | BOTTOMS | | | 593 | 621.8 | 11.0 | 214.0 | 3.4 |
| | | | RECOVERED | | | 3298 | 3311.7 | | | |
| | | | FEED CHARGED | | | 3298 | 3326.3 | 18.0 | 234.0 | 8.6 |
| | | | LOSS | | | −5 | 14.6 | | | |

TABLE 3B

Distillation Report for Feedstock B-btms
(FSL # 8691)
Feedstock B — Atmospheric distillation resid 650° F. + bottoms
Column Used: Sarnia HiVac

| CUT | VAPOR TEMP ST–END, ° F. | WEIGHT G | VOLUME ml @ 60° F. | API 60/60 | DENSITY 60° F. | WT PCT | VOL PCT | WT PCT | VOL PCT |
| --- | --- | --- | --- | --- | --- | --- | --- | --- | --- |
| 1 | 601–656 | 666.4 | 639 | 4.1 | 1.0435 | 20.12 | 19.38 | 20.03 | 19.40 |
| 2 | 656–702 | 666.9 | 646 | 5.6 | 1.0321 | 20.14 | 19.59 | 20.05 | 19.62 |
| 3 | 702–752 | 334.3 | 330 | 8.3 | 1.0122 | 10.09 | 10.01 | 10.05 | 10.02 |
| 4 | 752–800 | 167.7 | 173 | 14.5 | 0.9692 | 5.06 | 5.25 | 5.04 | 5.25 |
| 5 | 800–852 | 167.3 | 181 | 21.7 | 0.9236 | 5.05 | 5.49 | 5.03 | 5.50 |
| 6 | 852–900 | 167.1 | 181 | 21.9 | 0.9224 | 5.05 | 5.49 | 5.02 | 5.50 |
| 7 | 900–950 | 238.4 | 257 | 21.2 | 0.9267 | 7.25 | 7.79 | 7.17 | 7.80 |
| 8 | 950–976 | 85.4 | 91 | 18.9 | 0.9408 | 2.58 | 2.76 | 2.57 | 2.76 |
| 9 | 976–1000 | 80.8 | 85 | 18.2 | 0.9452 | 2.44 | 2.58 | 2.43 | 2.58 |
| 10 | 1000–1026 | 93.8 | 98 | 16.9 | 0.9535 | 2.83 | 2.97 | 2.82 | 2.98 |
| COL HOLDUP | | 4.0 | 4 | 3.4 | 1.0489 | 0.12 | 0.12 | 0.12 | 0.12 |
| BTMS | 1026+ | 621.8 | 593 | 3.4 | 1.0489 | 18.78 | 17.98 | 18.69 | 18.01 |
| EOR TRAPS | | 17.8 | 20 | | | | | 0.54 | 0.61 |
| TOTALS | | 3311.7 | 3298 | | | 100.00 | 100.00 | 99.56 | 100.15 |
| LOSS | | 14.6 | −5 | | | | | 0.44 | −0.15 |
| FEED | | 3326.3 | 3293 | 8.6 | 1.0100 | | | 100.00 | 100.00 |
| BACK CALCULATED API & DENSITY | | | | 9.4 | 1.0039 | | | | |

TABLE 4

Elemental Composition of Feedstock B
Analyses on Feedstock B Atmospheric Distillation 650 + F Resid

| Measured | Value |
| --- | --- |
| Nitrogen | 0.991 wt % |
| Sulfur | 0.863 wt % |
| Nickel | 8.61 ppm |
| Vanadium | <0.2 ppm |

Table 4 illustrates data from elemental analyses of Feedstock B atmospheric distillation (650+° F.) residue including some of the identified impurities. Table 4 displays the weight percent nitrogen, sulfur, nickel and vanadium present within this feedstock. These materials are removed in subsequent steps.

Step 3:

The higher diamondoids enriched by the separations of Step 2 were further treated to isolate a tetramantane fraction. In one case the distillation fraction 33 of Feedstock A (See FIG. 5 for a GC profile identifying this fraction.) was passed through a silica-gel gravity liquid chromatographic column (using cyclohexane elution solvent) to remove polar compounds and asphaltenes and concentrate higher diamondoids. The use of silver nitrate impregnated silica gel (10% by weight $AgNO_3$) provides cleaner diamondoid-containing fractions by removing the free aromatic and polar components. Higher diamondoids elute in the first eluting cyclohexane fraction off the column (before aromatic hydrocarbons appeared in the column eluent). While it is not necessary to use this chromatographic separation method, it facilitates subsequent steps.

Alternatively, pyrolysis products (as disclosed in Example 2) prepared using distillate fractions of Feedstock B could be passed through a silica-gel or $AgNO_3$ impregnated silica gel gravity liquid chromatography column to remove polar compounds and asphaltenes and concentrate higher diamondoids as described above. In either instance, the distillate fractions or the pyrolysis products could be purified using this step prior to subsequent isolation procedures.

Step 4:

The eluent from the column chromatography was analyzed by GC/MS to determine the approximate GC retention times of tetramantane isomers. Individual tetramantanes were assigned a number according to their elution order in the GCMS analysis. This number was used to identify individual tetramantanes in subsequent steps. Note that enantiomer pairs are not resolved in this analysis and so these enantiomers (racemic mixtures) were assigned a single number. GC retention times vary with changing columns and GC conditions and new reference retention time tables were prepared as needed using this procedure. Below is a table used in Example 4 procedures below.

| Tetramantane Reference # | 1 | 2 | 3 |
| --- | --- | --- | --- |
| GCMS Retention Times (Min.) | 11.28 | 11.84 | 12.36 |

Figure 6A:
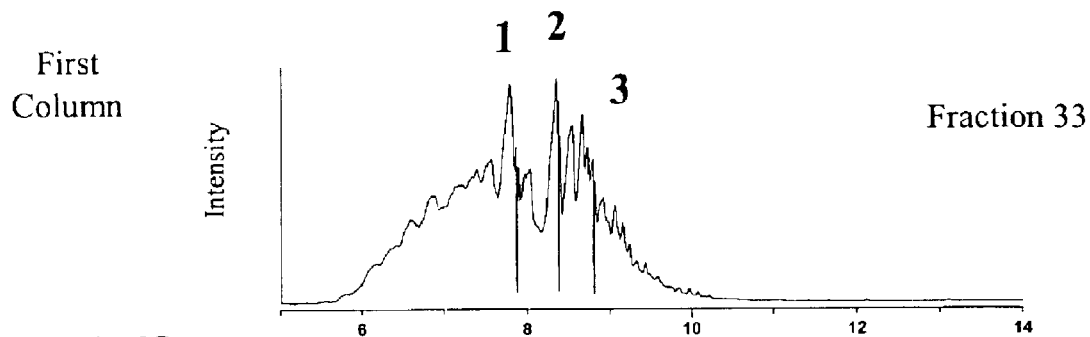
FIG. 6A, shows the first column cuts made on distillate fraction 33, Feedstock A. The bold face numbers refers to peaks of the tetramantanes.

Step 5:

A two-column preparative capillary gas chromatograph was then used to isolate tetramantanes from the distillate fractions cleaned-up by column chromatography. The cut times for the tetramantanes were set for the first preparative capillary GC column, methyl silicone DB-1, using the retention times and patterns from GC/MS analysis (from step 4 above). The results are shown in the top of FIG. 6A, identified as cuts 1, 2 and 3.

Figure 6B:
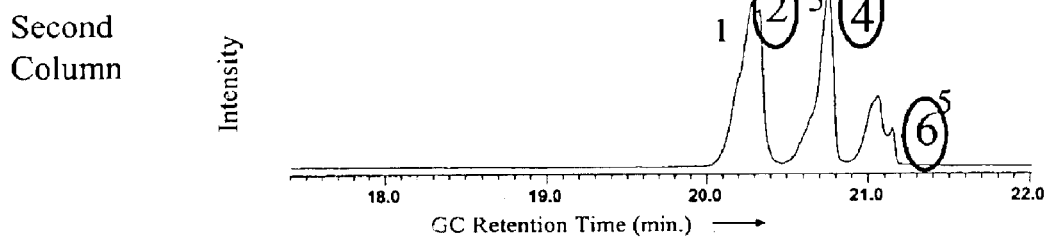
FIG. 6B, shows the second column peaks isolated and sent to the traps. The circled numbered peaks (2, 4, and 6) are the tetramantanes. It is noted that both enantiomers of the optically active tetramantane are contained within one of these peaks.

The first column was used to concentrate the tetramantanes by taking cuts that were then sent to the second column (see FIG. 6B). The second column, phenyl-methyl silicone a DB-17 equivalent, further separated and purified the tetramantanes and then sent them into individual vials (traps 1–6). GC trap fractions 2, 4 and 6 were collected and further processed.

Figure 7:
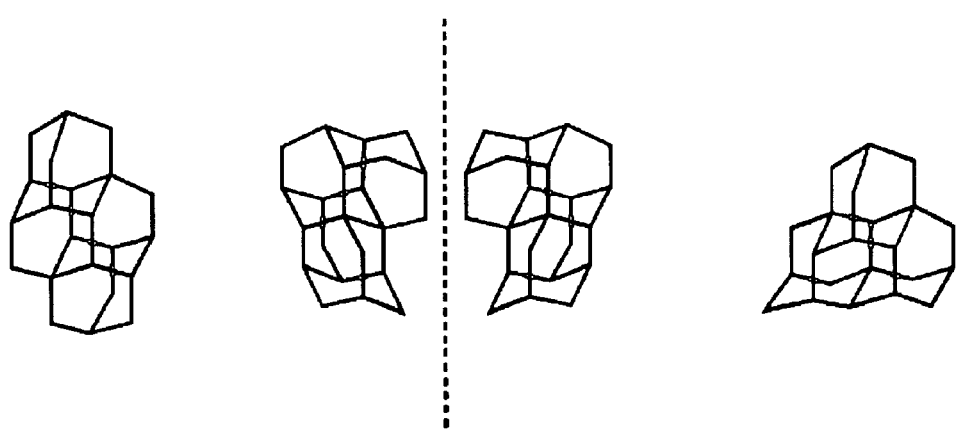
FIG. 7 illustrates the structures of the four-tetramantane isomers two of which are enantiomers.
Figure 8A:
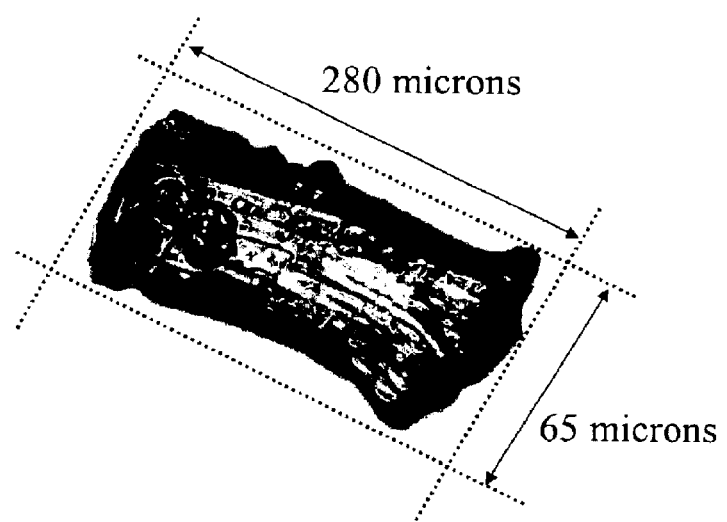
FIG. 8A was isolated from trap fraction 2, FIG. 8B was isolated from trap fraction 4, and FIG. 8C was isolated from trap fraction 6. Because the two enantiomeric tetramantanes have identical GC retentions times in FIG. 6, one of the crystals contains both enantiomers.
Figure 8B:
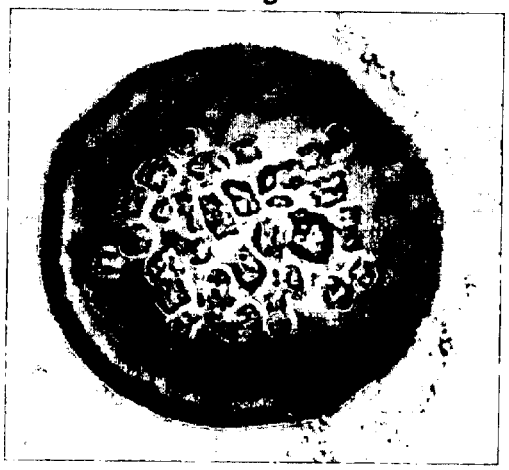
FIGS. 8(A, B, C) illustrates photomicrographs of tetramantane crystals isolated from Feedstock A by preparative gas chromatography (FIG. 6).
Figure 8C:
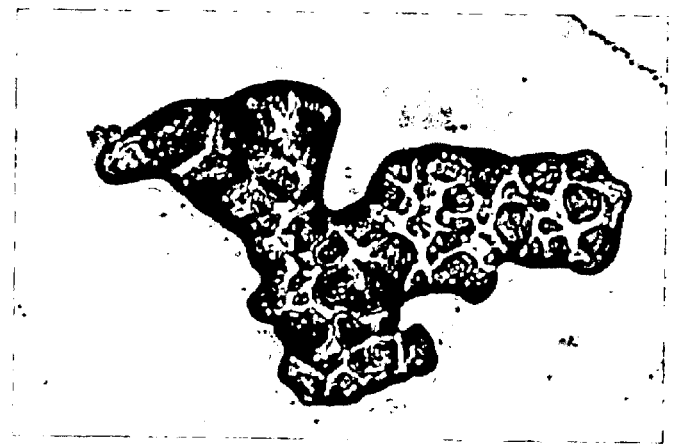

Step 6:

The highly concentrated tetramantanes were then allowed to crystallize from solution. Under the microscope at 30× magnification, crystals were visible in preparative GC trap fractions 2, 4, and 6 (see FIG. 6). Where concentrations were not high enough for crystallization to occur, further concentration by preparative GC was necessary. Structures of tetramantane isomers are shown in FIG. 7, including one, [123] tetramantane as two enantiomeric forms. FIGS. 8A, B and C illustrate photomicrographs of tetramantane crystals isolated from Feedstock A from preparative GC trap fraction #2, fraction #4 and fraction #6 corresponding to tetramantane 1, 2, and 3 (respectively).

Step 7:

After obtaining crystals of suitable size, material could be sent for structural determination using X-ray diffraction. Enantiomeric tetramantanes can undergo further separations to resolve their two components.

Example 2

Enrichment of Tetramantanes Using Pyrolysis

A pyrolysis method was developed to further purify distillate fractions such as distillate fractions #1–3 obtained from Feedstock B—Atmospheric distillation 650° F.+bottoms (Table 3 A/B) exploiting the great thermal stability of the tetramantanes relative to other crude oil components. FIG. 10(A,B,C) respectively, shows the GC profile of the distillate fractions #1–3 from Feedstock B—Atmospheric distillation 650° F.+bottoms (see FIG. 9 and Table 3A&B).

Removal of Nondiamondoids Using Pyrolysis

Figure 11:
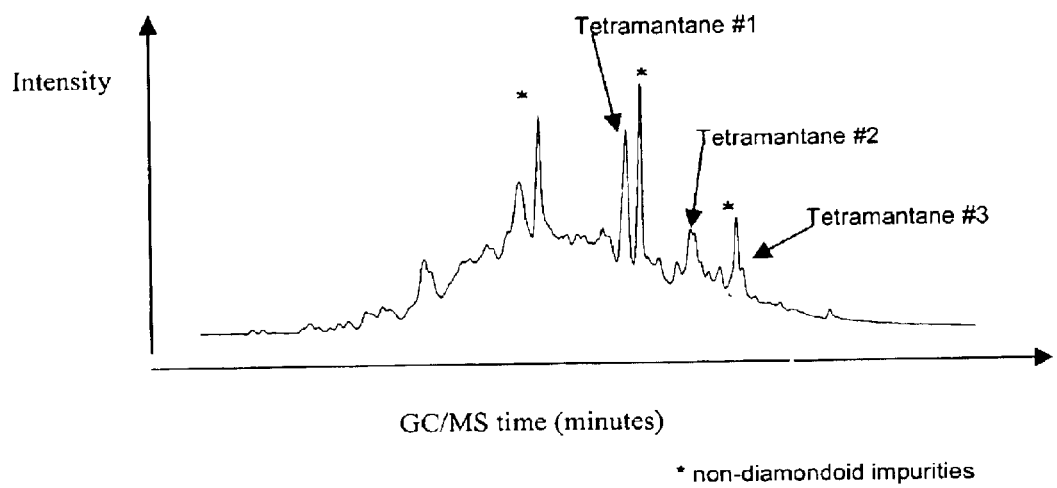
FIG. 11 illustrates the gas chromatogram of Feedstock B atmospheric distillation hold up fraction, exemplified in Example 1, which was used as feedstock in pyrolytic processing. The hold up fraction is the material recovered from the distillation column after distillation of Feedstock B at approximately 650° F. $T_1$, $T_2$ and $T_3$ indicate tetramantanes 1 to 3, respectively.
Figure 12:
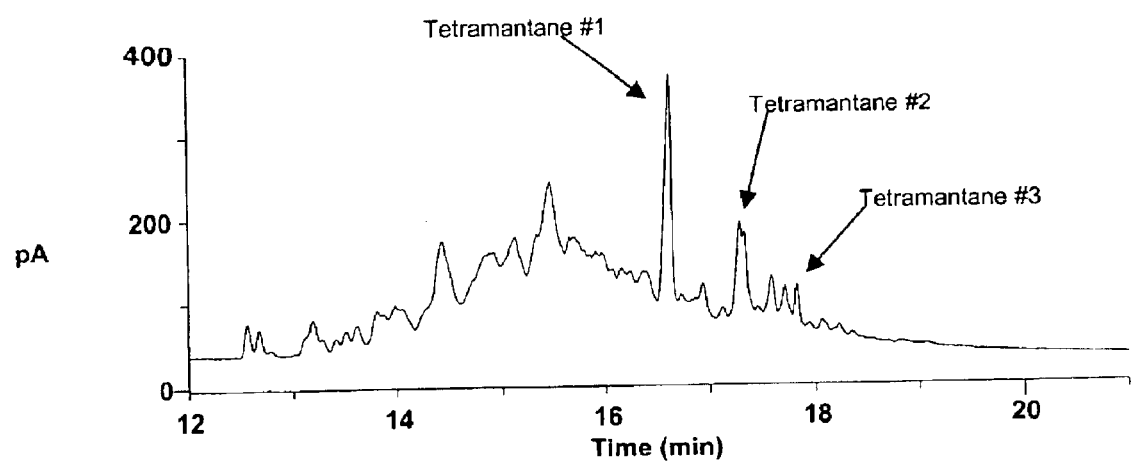
FIG. 12 illustrates the gas chromatogram of the pyrolytic product from the starting material in FIG. 11, i.e. the holdup fraction of Feedstock B atmospheric distillation 650° F.+bottoms, showing the degradation of nondiamondoid components.

This method used a reactor to pyrolyze and degrade a portion of the nondiamondoid components thereby enriching the diamondoids in the residue. Such reactors can operate at a variety of temperatures and pressures. FIGS. 11 and 12(A,B) illustrate this method and show a gas chromatogram of the Feedstock B 650° F.+distillation hold up before pyrolysis and the resulting pyrolysis product. The distillation hold up was the material rinsed from the distillation column after atmosphere distillation of Feedstock B. Prior to pyrolysis, the tetramantane peaks are obscured by the presence of nondiamondoid components (FIG. 11). Pyrolysis degraded the nondiamondoid components to easily removable gas and coke-like solids. As shown in FIG. 12, the tetramantane peaks are clearly visible after pyrolysis.

A PARR® reactor, from PARR INSTRUMENT COMPANY, Moline, Ill., was used to process the distillation fractions obtained from vacuum distillation of a feedstock. Pyrolysis was then conducted by heating the sample under vacuum in the reactor at 450° C. for 20.4 hours.

Example 3

Figure 13:
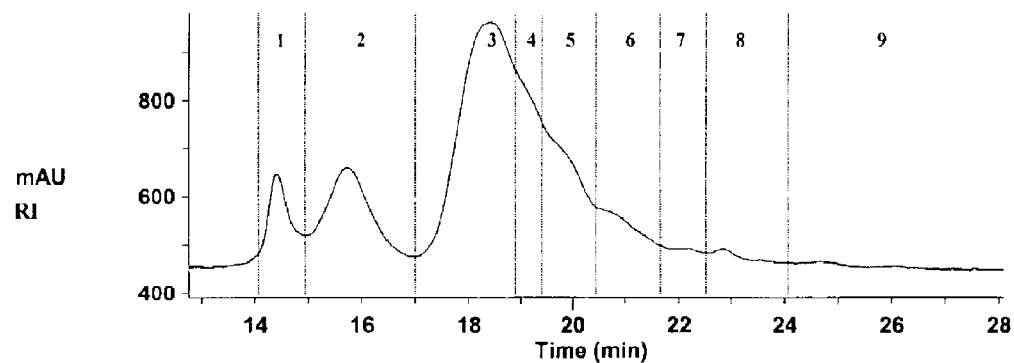
FIG. 13 illustrates the preparative HPLC trace of Feedstock A gas condensate distillation fraction #32 showing fractions taken (1–9).

Isolation of Tetramantanes Using HPLC
Isolations of Diamondoids Using HPLC In addition to the gas chromatographic and pyrolysis methods described above, HPLC was also shown to provide sufficient enrichments of some tetramantanes to allow for their crystallization. Suitable columns for use are well known to those skilled in the art. In some cases, reverse-phase HPLC with acetone as mobile phase can be used to effect this purification. A preparative HPLC run of Feedstock A, gas condensate distillate Fraction #32 was performed and the HPLC chromatogram recorded using a differential refractometer is shown in FIG. 13. Nine fractions where taken during the run as marked on FIG. 13. The HPLC columns used were two 25 cm×10 mm I.D. VYDAC octadecyl silane ODS columns operated in series (Vydac columns are manufactured by The Separations Group, Inc., CA, USA). A 20 microliter sample of a solution of Fraction #32 at 55 mg/ml was injected into the columns. The columns were set-up using acetone at 2.00 ml/min as a mobile phase carrier.

Figure 14A:
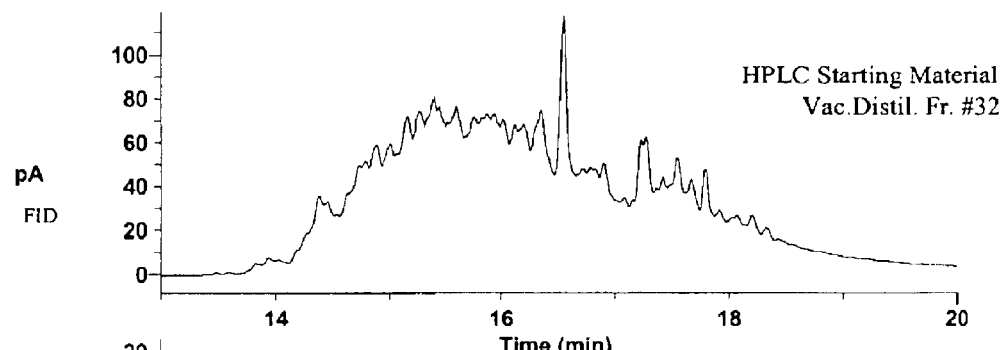
FIG. 14A illustrates a gas chromatogram of Feedstock A, distillate fraction #32, as compared to (FIG. 14B) its HPLC fraction #6 indicated as shown in FIG. 13. HPLC fraction #6 shows significant enrichment in one of the tetramantane components.
Figure 14B:
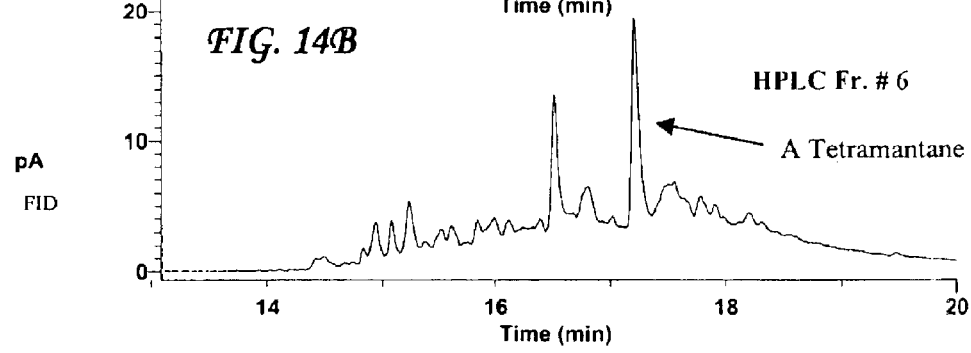
FIGS. 14(A, B) illustrates gas chromatograms showing enrichment in tetramantane.
Figure 15A:
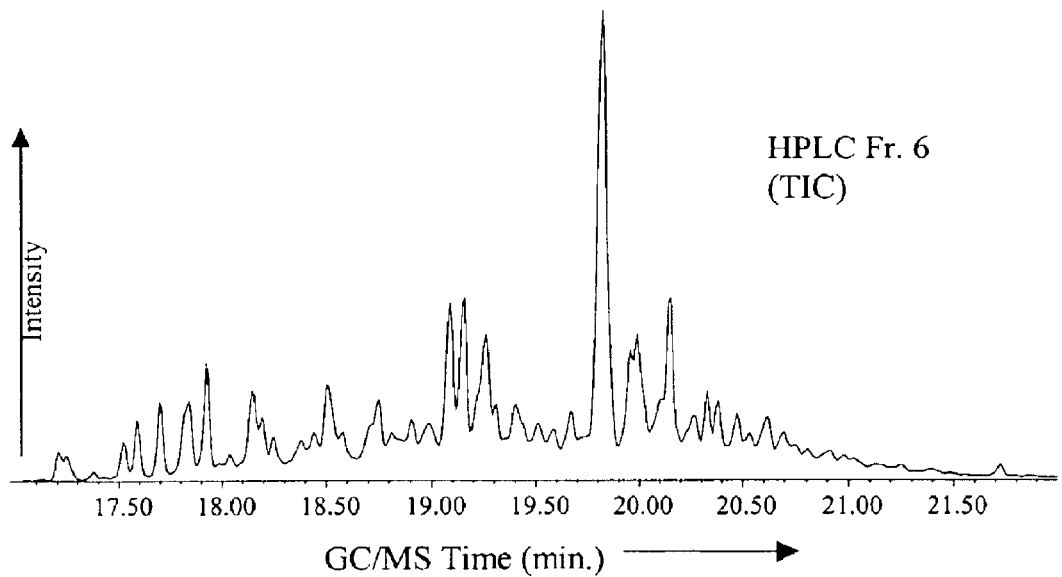
FIGS. 15(A, B) illustrates GC/MS total ion chromatogram (TIC) of HPLC fraction #6 (FIG. 13), showing one major component and selected ion chromatogram of fraction #6 (m/z 292) suggesting that this component is one of the tetramantane isomers.
Figure 15B:
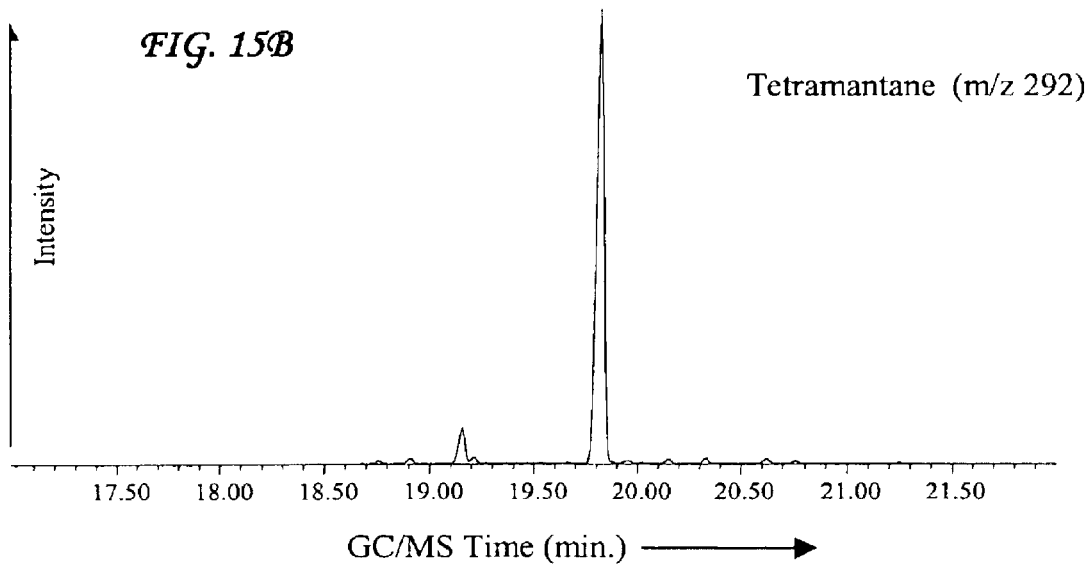

FIGS. 14(A,B) compares the gas chromatogram of the starting material (Feedstock A, distillation Fraction #32) and HPLC fraction #6, from FIG. 13. HPLC Fraction #6 is significantly enriched in tetramantane (see GC/MS FIG. 15). Tetramantane #2 in HPLC Fraction #6 is approaching a concentration sufficient to bring about its crystallization.

Example 4

Purification of Single Tetramantane Isomers

Figure 16:
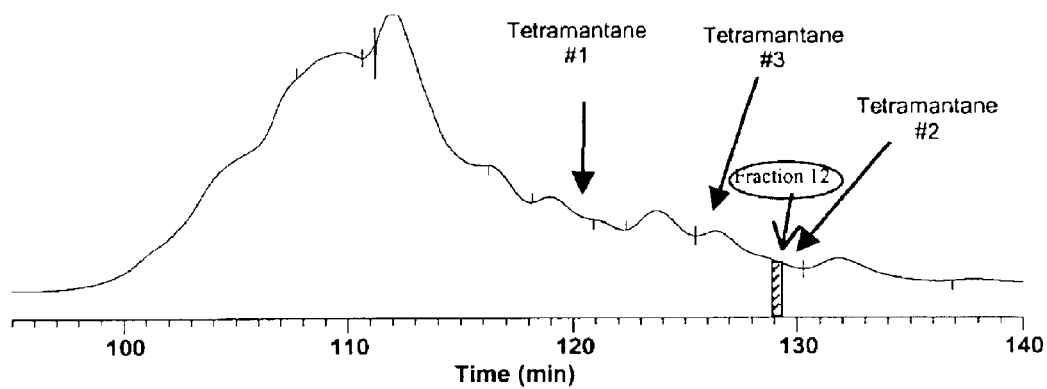
FIG. 16 illustrates a preparative HPLC isolation of the holdup fraction of Feedstock B atmospheric distillation 650° F.+bottoms, showing fractions taken at various retention times and the elution of the tetramantane components.

As shown in Example 3, tetramantanes can be isolated in high purity by using HPLC methods. In this example, HPLC columns of different specificities were used to isolate single tetramantane isomers. FIG. 16 shows a preparative separation of the tetramantanes using an octadecyl silane (ODS) HPLC column with acetone as a mobile phase of a distillation product as outlined in Example 1 as a feed stock. Specifically, a preparative HPLC isolation of the holdup fraction of Feedstock B atmospheric distillation 650° F.+bottoms was used to identify the retention times and elution of the tetramantane components. The first column was a Whatman M20 10/50 (×2) ODS with column operated in series using acetone at 5.00 ml/min as mobile phase (@590 psi), 0.500 ml injection, 56 mg/ml in acetone. The resulting chromatogram and the retention time fraction is noted on FIG. 16. Tetramantane #1 elutes first, tetramantane #3 elutes second and tetramantane #2 elutes last on the HPLC system (FIG. 16). The detector used was a differential refractometer. From this run, fraction 12 (FIG. 18) was taken for further purification.

Figure 17:
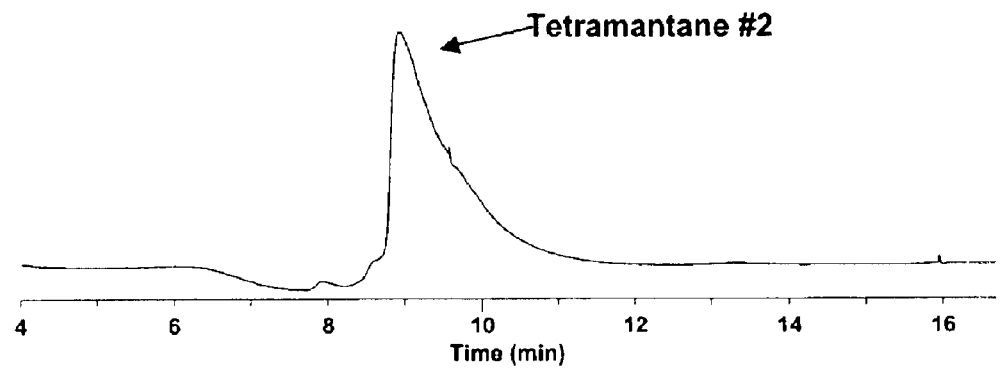
FIG. 17 illustrates the HPLC chromatogram of fraction 12 (FIG. 16) run on HYPERCARB stationary phase with acetone mobile phase resulting in the isolation of tetramantane 2.
Figure 19A:
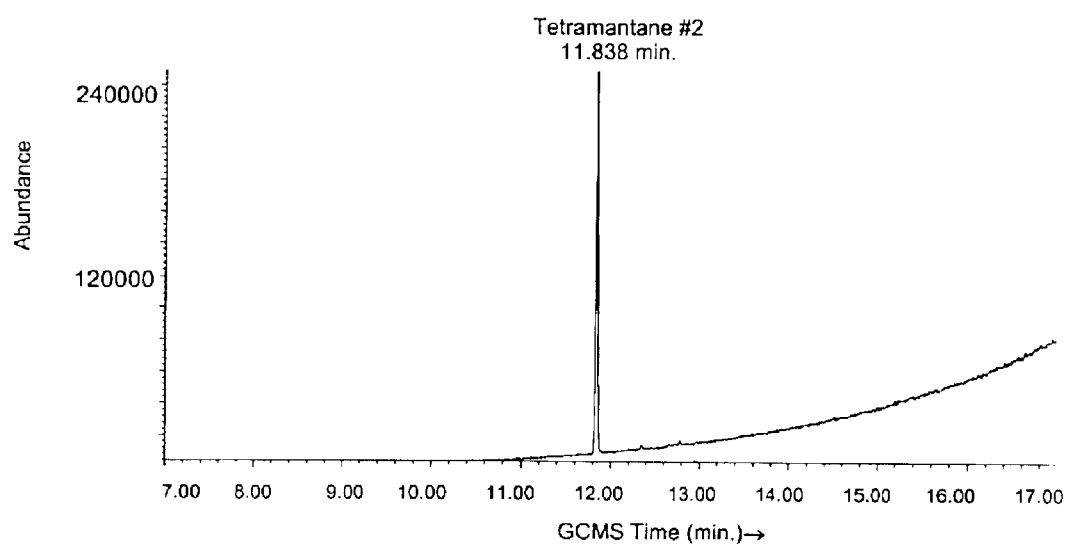
FIGS. 19(A, B) illustrates GC/MS total ion chromatogram (TIC) and mass spectrum of tetramantane #2 isolated by using two different HPLC columns.

Further purification of fraction 12 was achieved using HYPERCARB-S HPLC columns having a different specificity than the ODS column above, to isolate tetramantane #2. The HYPERCARB-S column (manufactured by Thermo Hypersil, Penn, USA), 4.6 mm I.D.×250 mm, operated in series using acetone at 1.00 mL/min as mobile phase (@180 psi), 50 microliter injection of 4 mg/ml in acetone also using a differential refractometer. Tetramantane #3 elutes first, tetramantane #1 elutes second and tetramantane #2 elutes last on this HYPERCARB HPLC system. The HYPERCARB HPLC chromatogram of fraction 12 is shown in FIG. 17. The purified tetramantane #2 was cut from this HPLC run and is illustrated in FIGS. 19A and B. HYPERCARB HPLC runs on ODS HPLC cut led to isolation of the remaining tetramantanes.

Figure 18A:
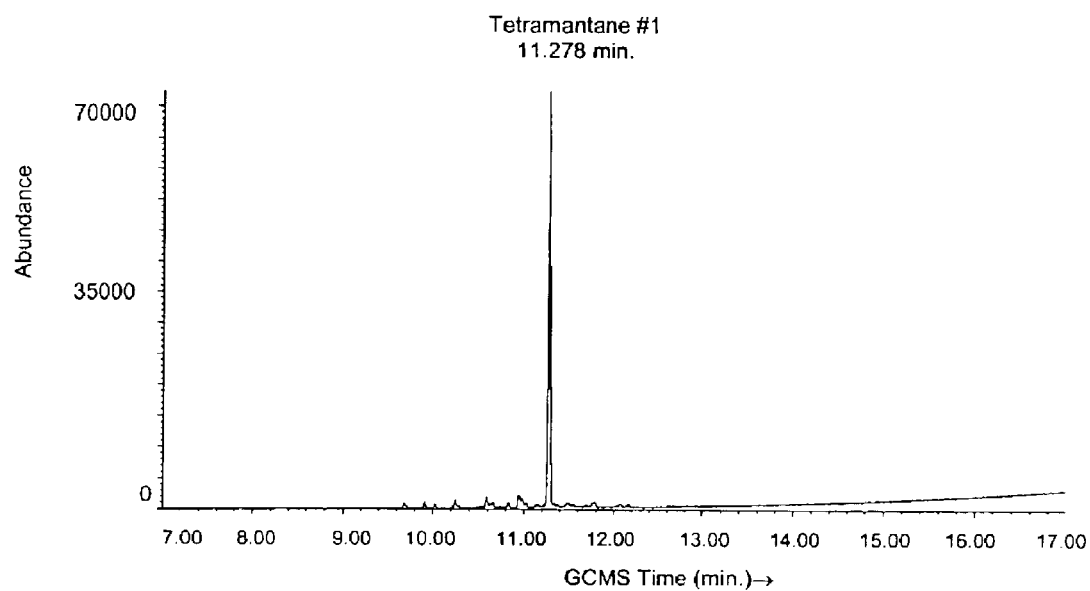
FIGS. 18(A, B) illustrates GC/MS total ion chromatogram (TIC) and mass spectrum of tetramantane #1 isolated by using two different HPLC columns.
Figure 18B:
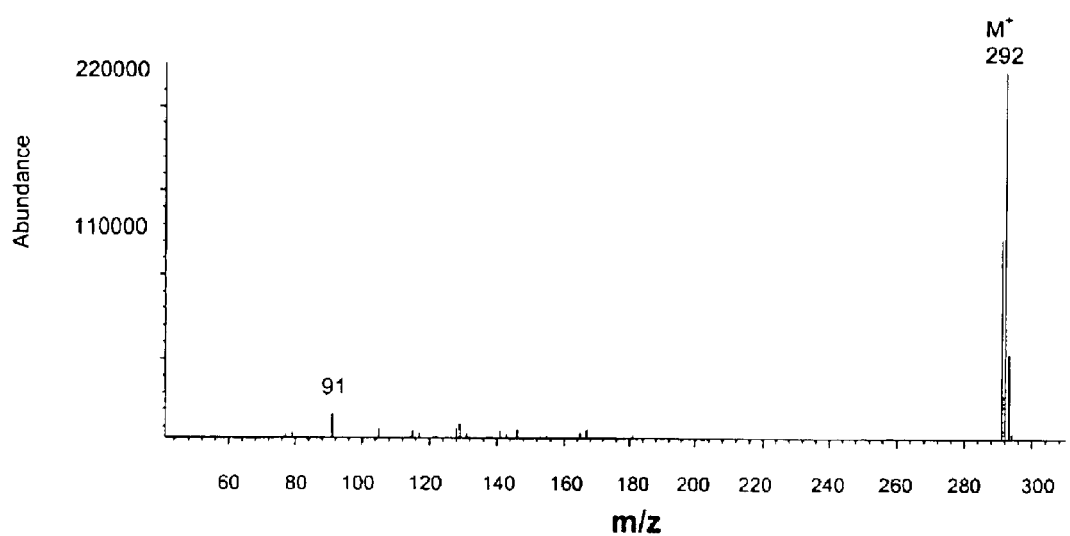
Figure 19B:
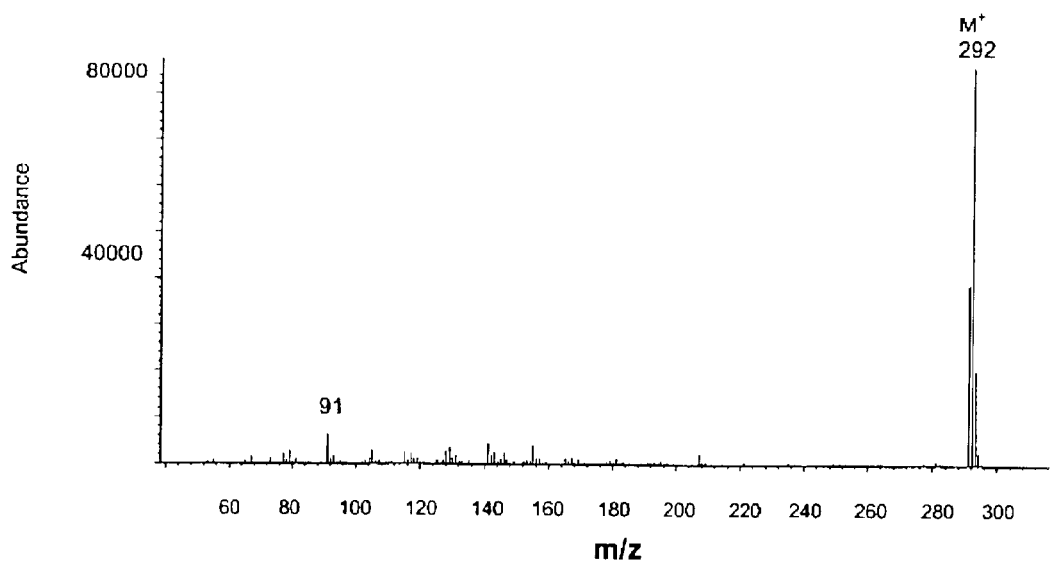
Figure 20A:
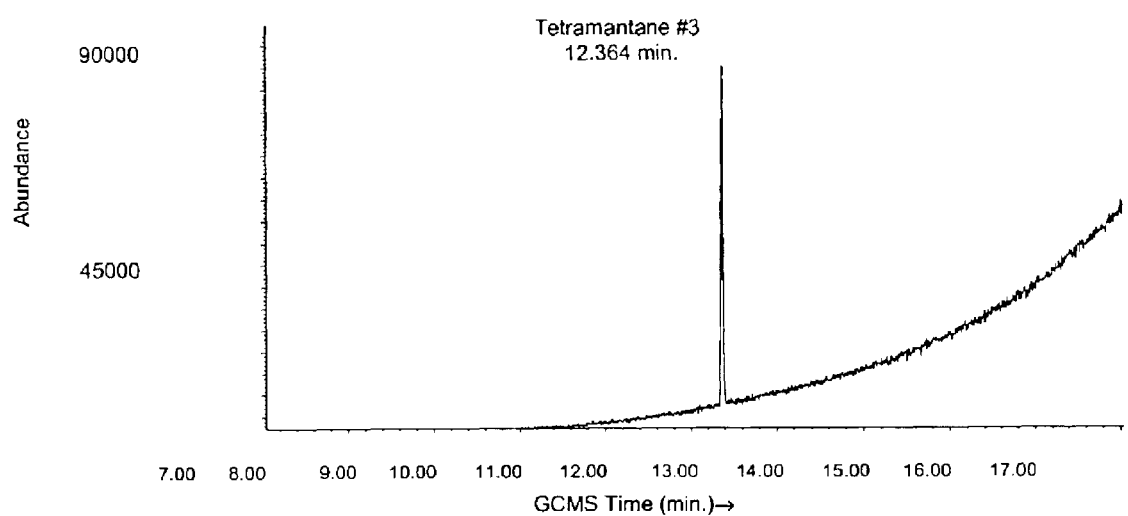
FIGS. 20(A, B) illustrates GC/MS total ion chromatogram (TIC) and mass spectrum of tetramantane #3 isolated by using two different HPLC columns.
Figure 20B:
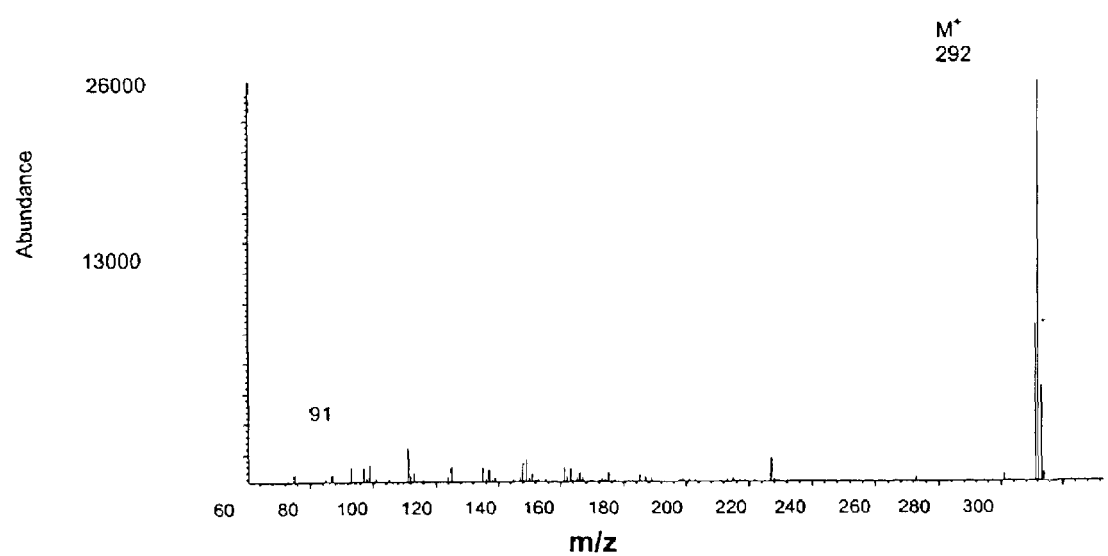
Figure 21:
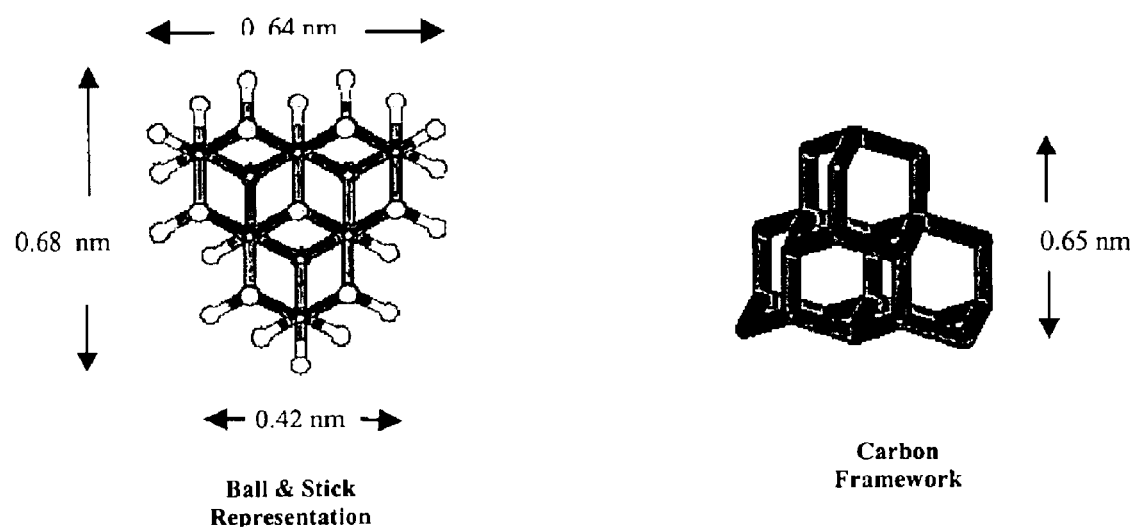
FIGS. 21–28 illustrates the size and structure with views into various diamond crystal lattice planes for the iso-, skew-, and anti-tetramantane isomers.
Figure 21:
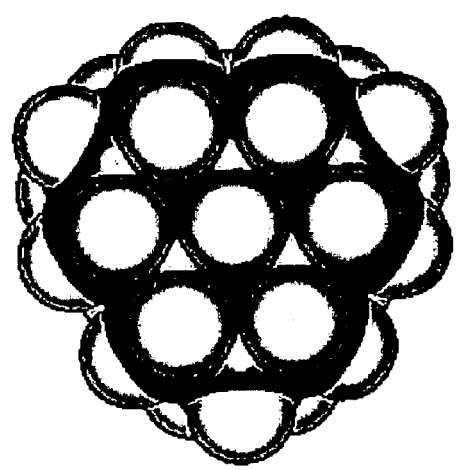
Figure 22:
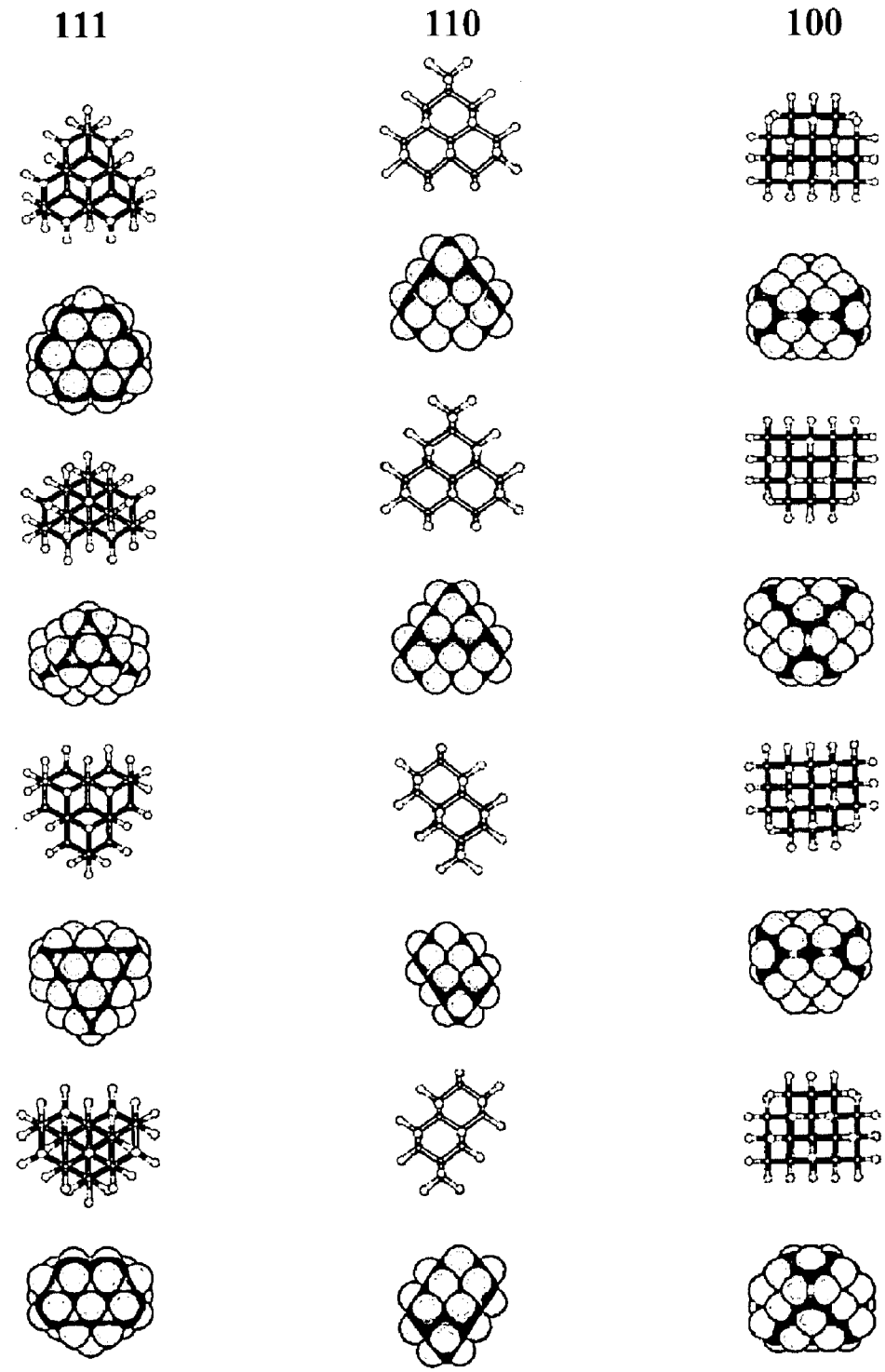
Figure 23:
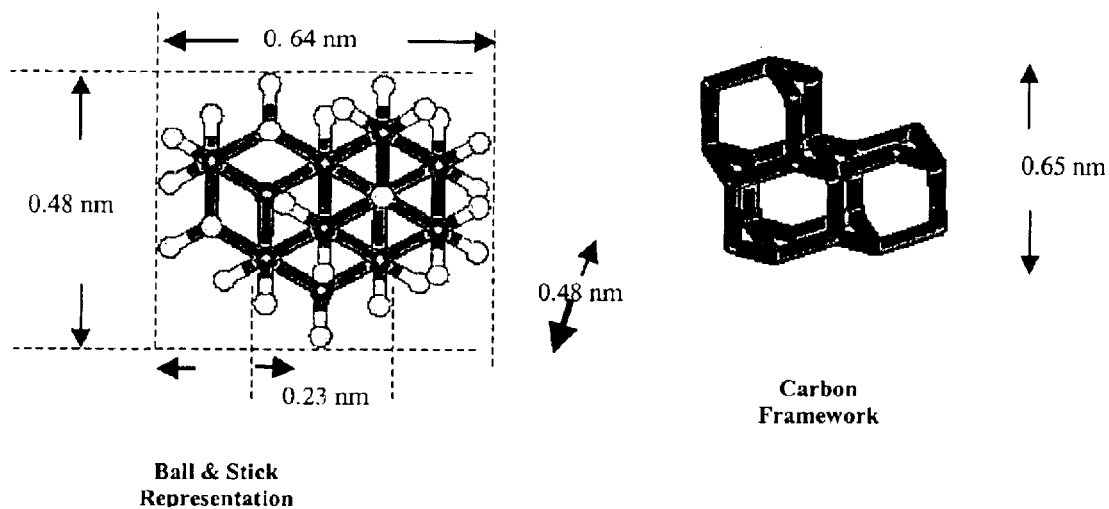
Figure 23:
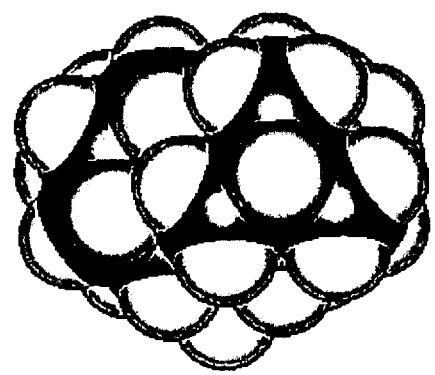
Figure 24:
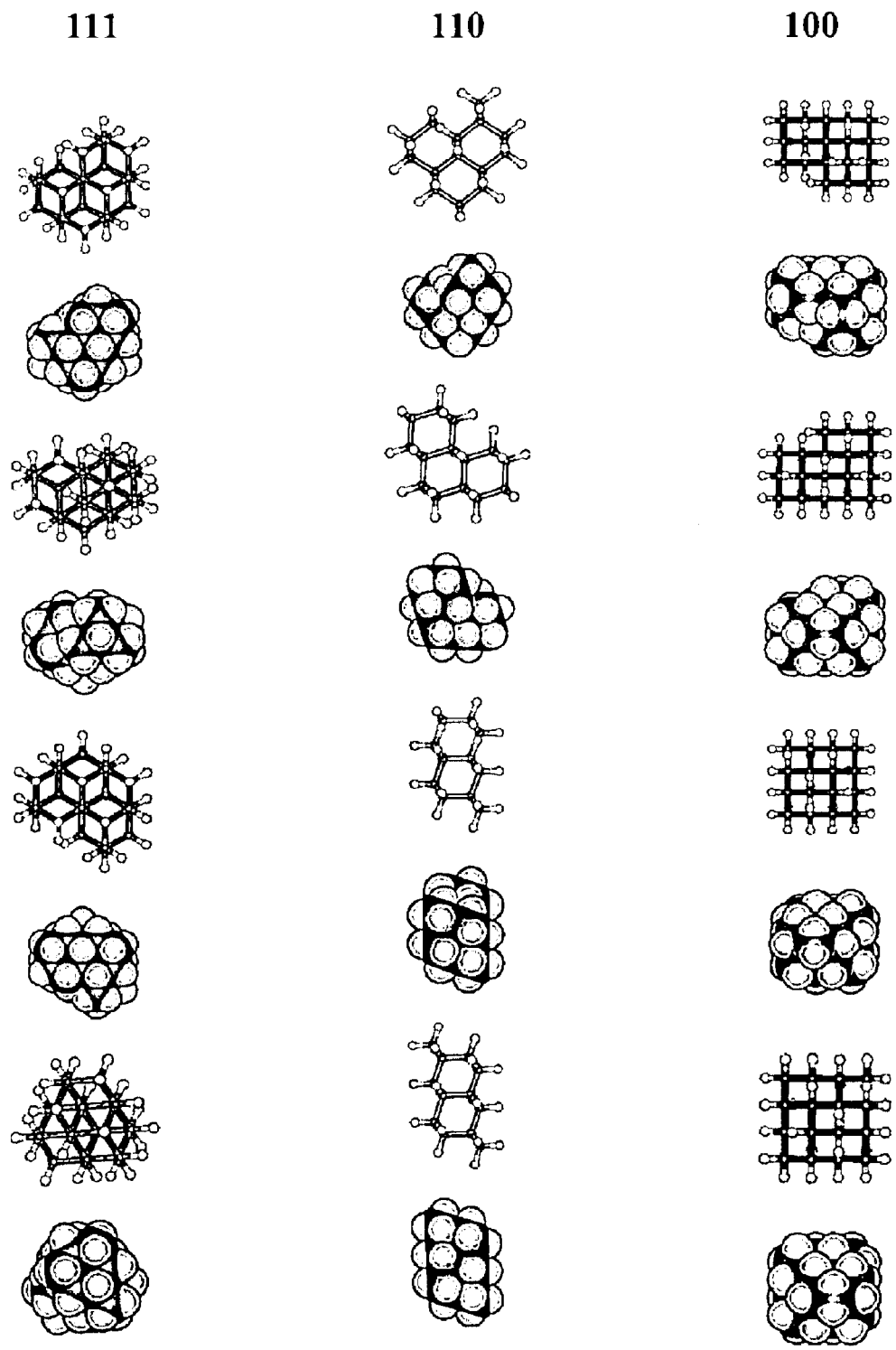
Figure 25:
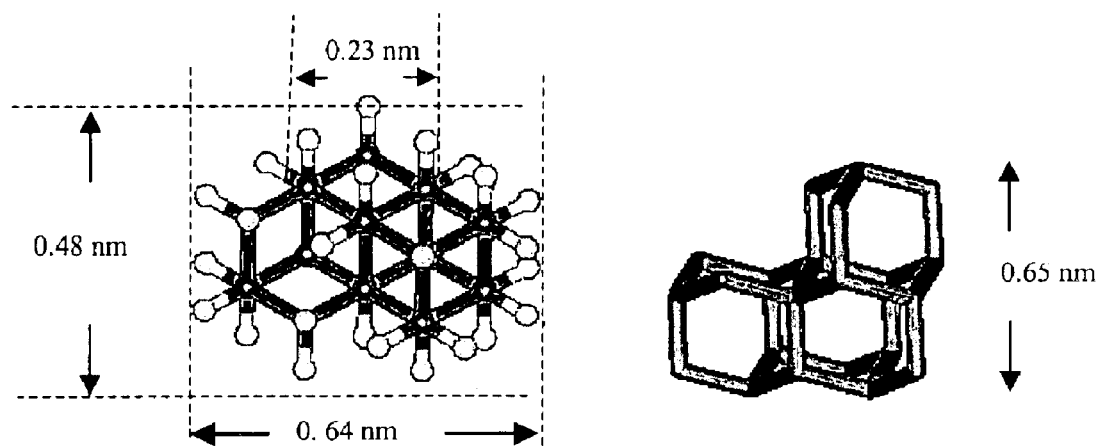
Figure 25:
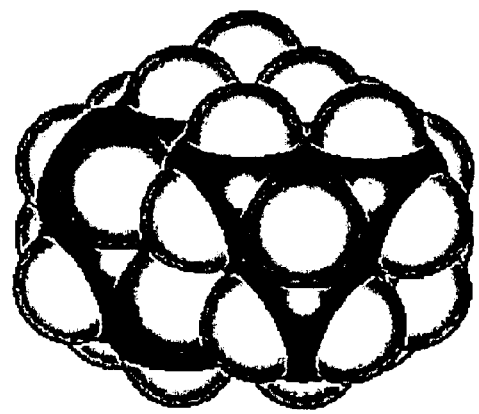
Figure 26:
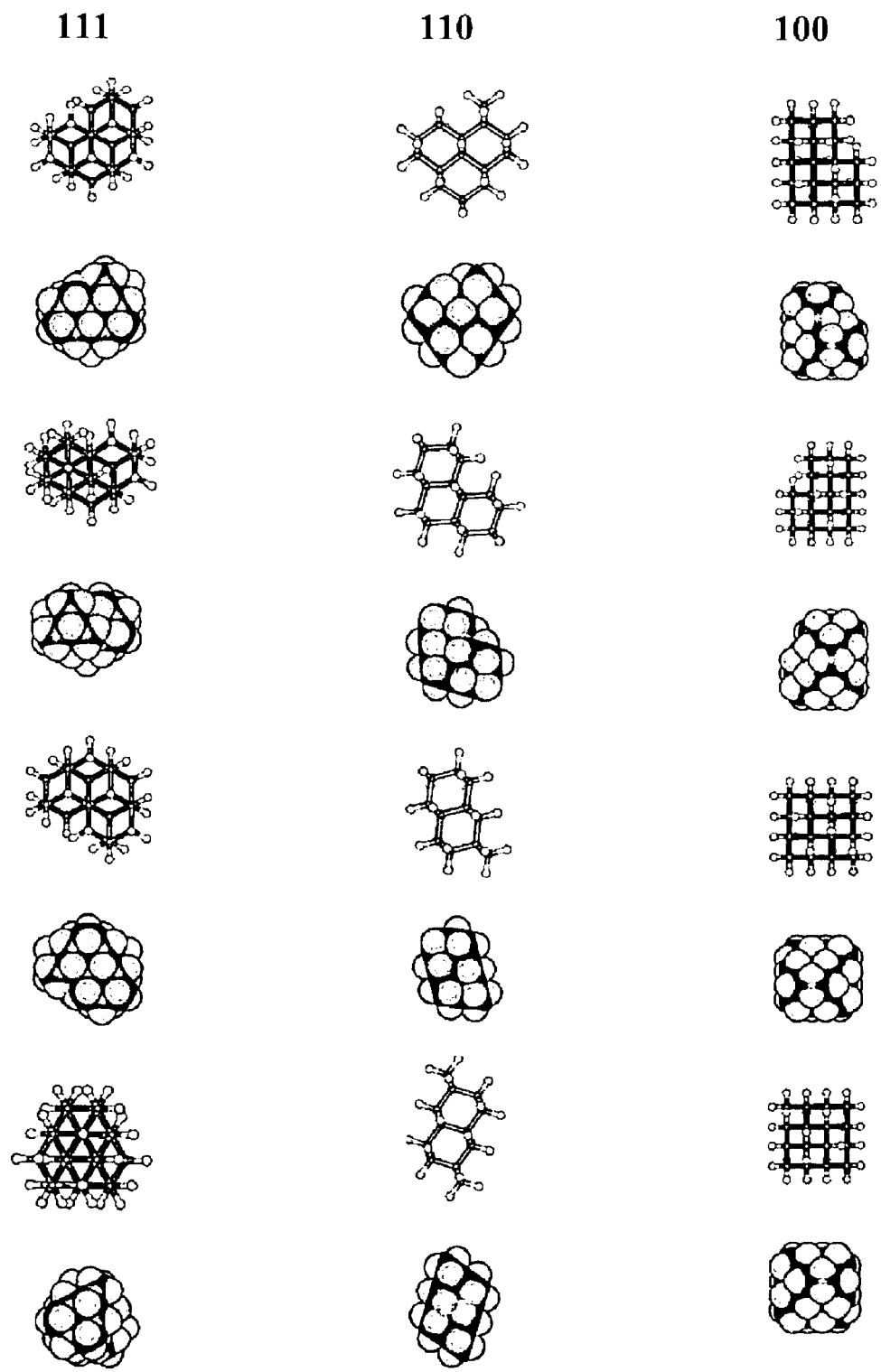
Figure 27:
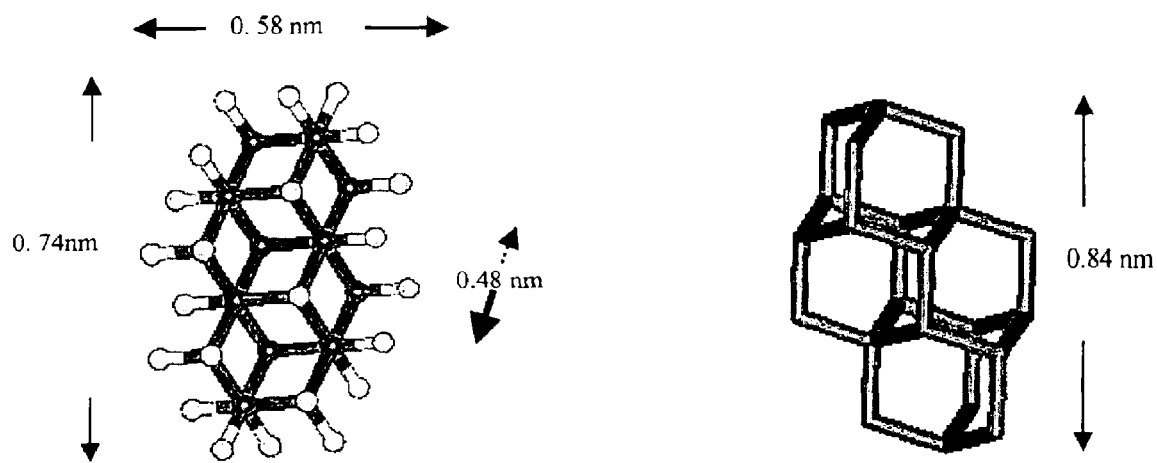
Figure 27:
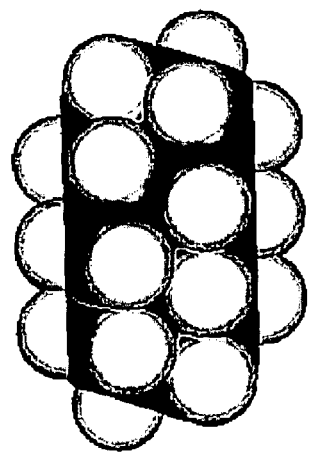
Figure 28:
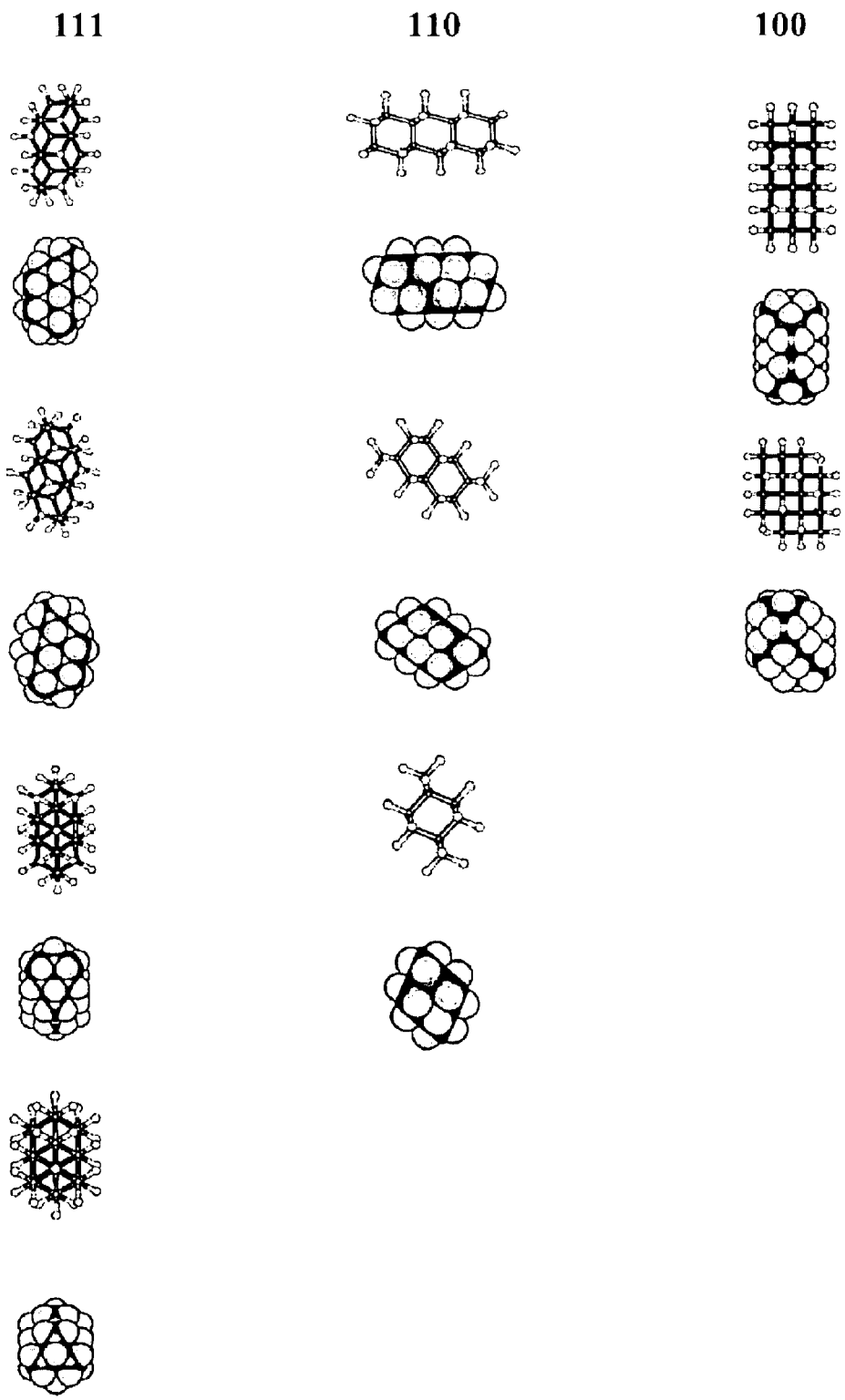

The different separation selectivity facilitates isolation of tetramantanes; which are shown in FIGS. 18 through 20. FIG. 18A shows the GC/MS total ion chromatogram (TIC) of an HPLC fraction containing tetramantane #1; and below, FIG. 18B shows the mass spectrum. FIG. 19A shows the GC/MS total ion chromatogram (TIC) of an HPLC fraction containing isolated tetramantane #2; and below FIG. 19B shows the mass spectrum. FIG. 20 shows the GC/MS total ion chromatogram (TIC) of an HPLC fraction containing isolated tetramantane #3; and below FIG. 20B shows the mass spectrum.

Figure 29:
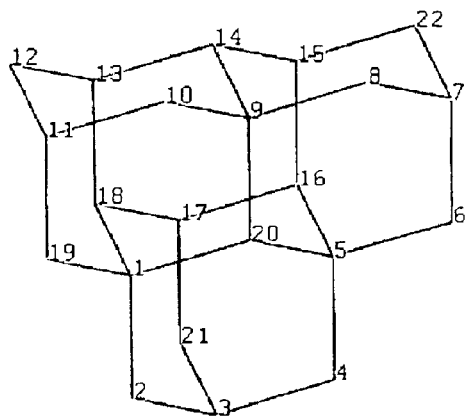
FIG. 29 illustrates the Von Baeyer numbering scheme for each tetramantane.
Figure 29:
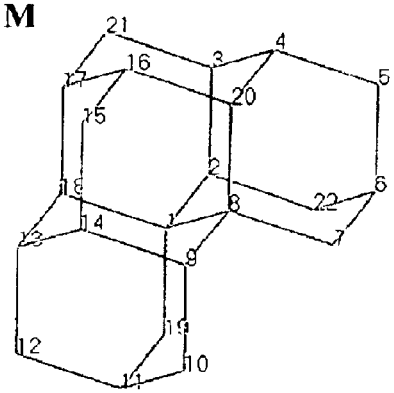
Figure 29:
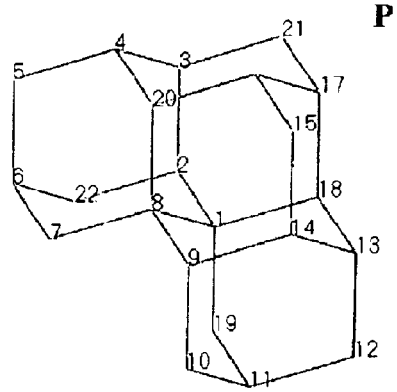
Figure 29:
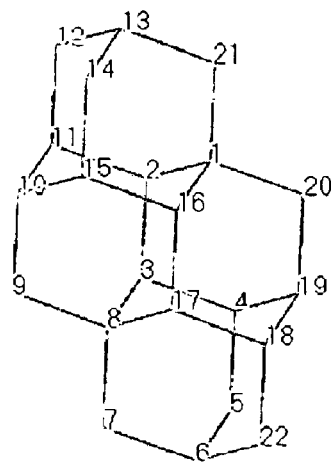

FIGS. 21 through 28 illustrate the size and structure with views into various diamond crystal lattice planes for the iso-, skew-, and anti-tetramantane isomers. FIG. 29 illustrates the Von Baeyer numbering for the tetramantanes.

Example 5

Isolation of Substituted Tetramantanes

Substituted tetramantanes also naturally occurring and are present in Feedstocks A and B. These natural occurring substituted tetramantanes have uses similar to the unsubstituted tetramantanes and de-alkylated to yield the corresponding unsubstituted tetramantanes. Accordingly, methods for the isolation of individual substituted tetramantanes were devised and exemplified by the isolation of alkyl substituted compounds.

Figure 30:
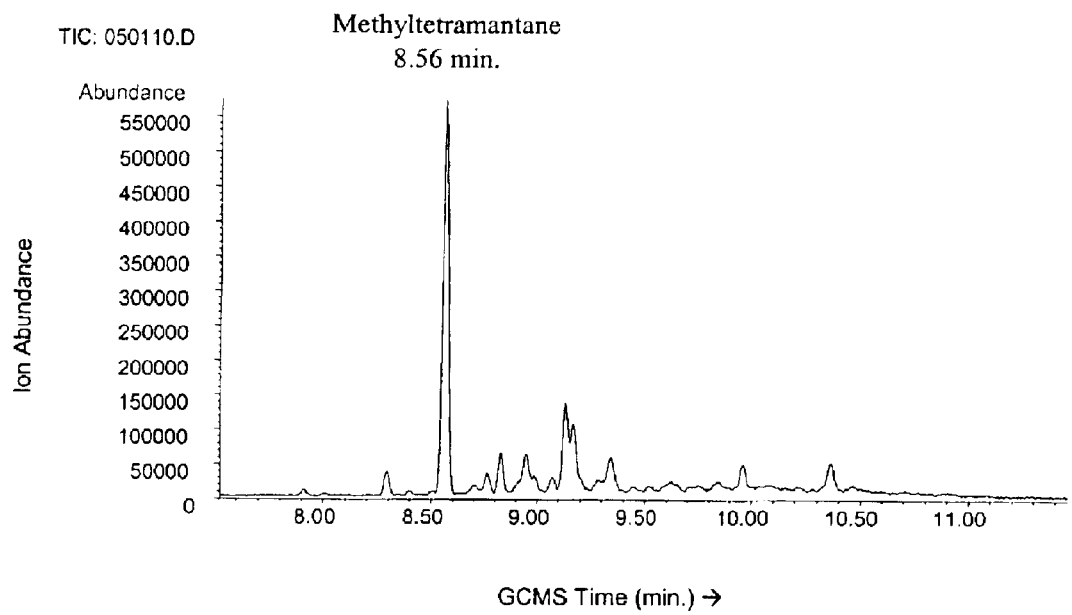
FIGS. 30(A, B) illustrates GC/MS total ion chromatogram (TIC) and mass spectrum of a methyltetramantane purified by ODS HPLC.
Figure 30:
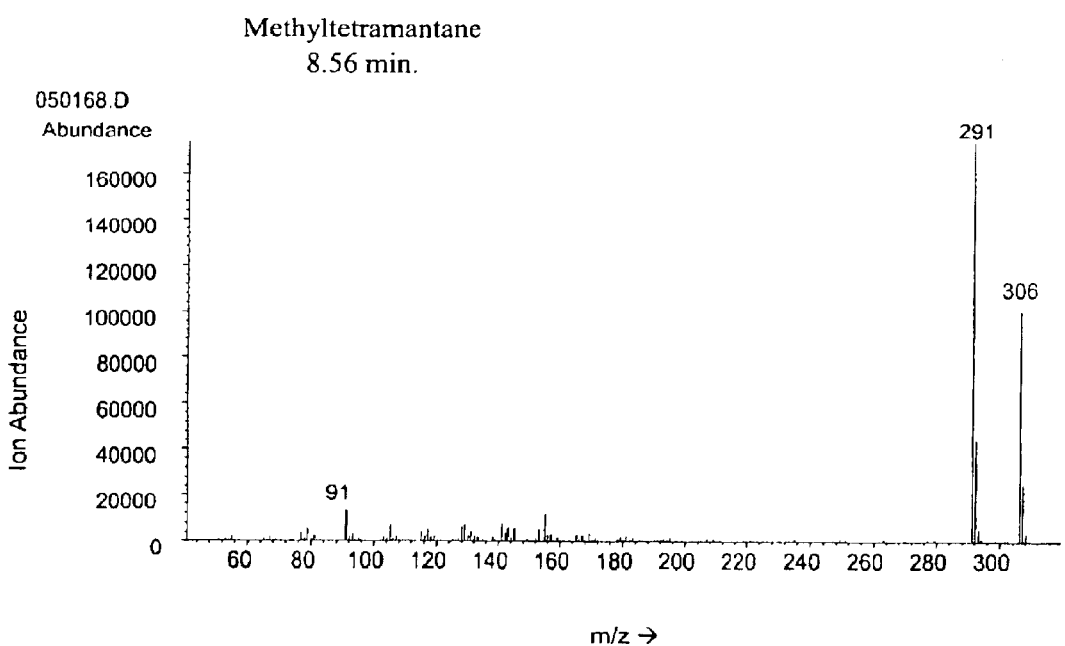

Alkyltetramantanes can be purified using methodologies described for nonalkylated tetramantanes given in Examples 3 and 4. One type of monomethylated tetramantane has a molecular weight of 306 (yielding a mass spectrometric molecular ion of m/z 306, and shows a mass spectrometric loss of the methyl group giving the m/z 291 mass spectrometric fragment ion indicative of a tetramantane moiety (FIG. 30). This alkylated compound was enriched in ODS HPLC fraction #10 with a retention time of 8.56 minutes in our GC/MS system and could be further purified to form a crystal. When more than one alkyltetramantane is present it is isolated using ODS or Hypercard columns, an additional HPLC separation, or alternative by a preparative GC procedure (as is Example 3) to yield high purity alkyltetramantanes.

What is claimed is:

1. A composition comprising diamondoids wherein at least about 50 weight percent of the diamondoids are one or more tetramantane components, with the proviso that when there is only one tetramantane component it is not unsubstituted anti-tetramantane.

2. A composition of claim 1 wherein from 50 to 100 weight percent of the diamondoids are one or more tetramantane components.

3. A composition of claim 1 wherein from 70 to 100 weight percent of the diamondoids are one or more tetramantane components.

4. A composition of claim 1 wherein from 95 to 100 weight percent of the diamondoids are one or more tetramantane components.

5. A composition of claim 1 wherein from 99 to 100 weight percent of the diamondoids are one or more tetramantane components.

6. The composition of any of claims 1–5, wherein the one or more tetramantane components are a single tetramantane component.

7. The composition of any of claim 6 wherein the single tetramantane component is iso-tetramantane.

8. The composition of any of claim 6, wherein the single tetramantane component is skew-tetramantane.

9. The composition of any of claim 6, wherein the single tetramantane component is a single enantiomer of skew-tetramantane.

10. The composition of any of claims 1–5 wherein the tetramantane components comprise substituted tetramantane components.

11. The composition of any of claim 10 wherein the substituted tetramantane components comprise substituted tetramantane components having from 1 to 10 alkyl substituents.

12. A composition comprising at least about 10% by weight of one or more tetramantane components selected from iso-tetramantane and the skew-tetramantane.

13. The composition of claim 12 containing from 50 to 100% by weight of one or more tetramantane components.

14. The composition of claim 12 containing from 70 to 100% by weight of one or more tetramantane components.

15. The composition of claim 12 containing from 95 to 100% by weight of one or more tetramantane components.

16. The composition of claim 12 containing from 99 to 100% by weight of one or more tetramantane components.

17. The composition of claim 1, wherein the one or more tetamantane components include iso-tetramantane.

18. The composition of claim 1, wherein the one or more tetramantane components include skew-tetramantane enantiomer A.

19. The composition of claim 1, wherein the one or more tetramantane components include skew-tetramantane enantiomer B.

20. The composition of claim 1, wherein the one or more tetramantane components are in crystalline form.

21. A process for recovering a composition enriched in one or more tetramantane components which process comprises:
   a. selecting a feedstock comprising recoverable amounts of tetramantane components and nontetramantane components;
   b. removing from the feedstock a sufficient amount of nontetramantane components having boiling points less than the lowest boiling point tetramantane component under conditions to form a treated feedstock enriched in tetramantane components which can be recovered;
   c. recovering a composition enriched in one or more tetramantane components from said treated feedstock formed in b) above with one or more additional separation techniques selected from the group consisting of chromatographic techniques, thermal diffusion techniques, zone refining, progressive recrystallization and size separation techniques.

22. A process for recovering a composition enriched in tetramantane components which process comprises:
   a. selecting a feedstock comprising recoverable amounts of tetramantane components and nontetramantane components;
   b. removing from the feedstock a sufficient amount of nontetramantane components having a boiling point less than the lowest boiling point tetramantane component under conditions to form a treated feedstock enriched in tetramantane components which can be recovered;
   c. thermally degrading said treated feedstock to pyrolyze at least a sufficient amount of nondiamondoid components therefrom under conditions to form a thermally treated feedstock retaining recoverable amounts of tetramantane components;
   d. recovering a composition enriched in one or more tetramantane components from said thermally treated feedstock formed in c) above with one or more additional separation techniques selected from the group consisting of chromatographic techniques, thermal diffusion techniques, zone refining, progressive recrystallization and size separation techniques.

23. A process for recovering a composition enriched in one or more tetramantane components which process comprises:
   a. selecting a feedstock comprising recoverable amounts of tetramantane components;
   b. thermally degrading said feedstock to pyrolyze at least a sufficient amount of nondiamondoid components therefrom under conditions to provide a thermally treated feedstock retaining recoverable amounts of tetramantane;
   c. removing from the thermally treated feedstock a sufficient amount of components having a boiling point less than the lowest boiling point of tetramantane component under conditions to form a treated feedstock enriched in tetramantanes components which can be recovered;
   d. recovering a composition enriched in one or more tetramantane components from said treated feedstock recovered in c) above with one or more additional separation techniques selected from the group consisting of chromatographic techniques, thermal diffusion techniques, zone refining, progressive recrystallization and size separation techniques.

24. A process for recovering a composition enriched in one or more tetramantane components which process comprises:
   a. selecting a feedstock comprising recoverable amounts of tetramantane components and nontetramantane components;
   b. fractionating the feedstock to form one or more cuts enriched in materials having boiling points in the range of from just below the boiling point of the lowest boiling tetramantane component to just above the boiling point of the highest boiling tetramantane component;
   c. recovering a composition enriched in one or more tetramantane components from said one or more cuts formed in b) above with one or more additional separation techniques selected from the group consisting of chromatographic techniques, thermal diffusion techniques, zone refining, progressive recrystallization and size separation techniques.

25. A process for recovering a composition enriched in one or more tetramantane components which process comprises:
   a. selecting a feedstock comprising recoverable amounts of tetramantane components and nontetramantane components;
   b. fractionating the feedstock to form one or more cuts enriched in materials having boiling points in the range of from just below the boiling point of the lowest boiling tetramantane component to just above the boiling point of the highest boiling tetramantane component;
   c. thermally degrading one or more cuts said to pyrolyze at least a sufficient amount of nondiamondoid components therefrom under conditions to form one or more thermally treated cuts retaining recoverable amounts of tetramantane;
   d. recovering a composition comprising one or more tetramantane components from one or more said thermally treated cuts formed in c) above with one or more additional separation techniques selected from the group consisting of chromatographic techniques, thermal diffusion techniques, zone refining, progressive recrystallization and size separation techniques.

26. A process for recovering a composition enriched in one or more tetramantane components which process comprises:
   a. selecting a feedstock comprising recoverable amounts of tetramantane components;
   b. thermally degrading said feedstock to pyrolyze at least a sufficient amount of nondiamondoid components therefrom under conditions to provide a thermally treated feedstock retaining recoverable amounts of tetramantane;
   c. fractionating the thermally treated feedstock to form one or more cuts enriched in materials having boiling points in the range of from just below the boiling point of the lowest boiling tetramantane component to just above the boiling point of the highest boiling tetramantane component;
   d. recovering a composition enriched in one or more tetramantane components from one or more cuts formed c) above with one or more additional separation techniques selected from the group consisting of chromatographic techniques, thermal diffusion techniques, zone refining, progressive recrystallization and size separation techniques.

27. The process according to any of claims 24–26 wherein said boiling point range is a range having atmospheric equivalents of between about 300 to about 430° C.

28. The process according to any of claims 21–26 wherein said separation technique is a chromatographic technique.

29. The process according to claim 28 wherein said chromatographic technique is selected from the group consisting of liquid chromatography, preparative gas chromatography and high performance liquid chromatography.

30. The process according to claim 28 wherein said additional separation technique is high performance liquid chromatography comprising one or more high performance liquid chromatography columns.

31. The process according to claim 30 wherein the high performance liquid chromatography columns are selected to have a different specificity to the tetramantane components.

32. A product prepared by the process of claim 21.
33. A product prepared by the process of claim 22.
34. A product prepared by the process of claim 23.
35. A product prepared by the process of claim 24.
36. A product prepared by the process of claim 25.
37. A product prepared by the process of claim 26.

* * * * *